(12) United States Patent
Bolling

(10) Patent No.: US 9,192,471 B2
(45) Date of Patent: Nov. 24, 2015

(54) DEVICE FOR TRANSLUMENAL RESHAPING OF A MITRAL VALVE ANNULUS

(75) Inventor: Steven F. Bolling, Ann Arbor, MI (US)

(73) Assignee: MILLIPEDE, INC., Santa Rosa, CA (US)

( * ) Notice: Subject to any disclaimer, the term of this patent is extended or adjusted under 35 U.S.C. 154(b) by 1011 days.

(21) Appl. No.: 11/620,955

(22) Filed: Jan. 8, 2007

(65) Prior Publication Data

US 2008/0167713 A1    Jul. 10, 2008

(51) Int. Cl.
*A61F 2/06* (2013.01)
*A61F 2/24* (2006.01)
*A61B 17/00* (2006.01)
*A61B 17/064* (2006.01)
(Continued)

(52) U.S. Cl.
CPC ......... *A61F 2/2445* (2013.01); *A61B 17/00234* (2013.01); *A61B 17/068* (2013.01); *A61B 17/0644* (2013.01); *A61F 2/2466* (2013.01); *A61B 17/0401* (2013.01); *A61B 2017/00243* (2013.01); *A61B 2017/00783* (2013.01); *A61B 2017/00862* (2013.01); *A61B 2017/00867* (2013.01); *A61B 2017/0409* (2013.01); *A61B 2017/0414* (2013.01); *A61B 2017/0647* (2013.01); *A61B 2017/12018* (2013.01); *A61F 2/243* (2013.01)

(58) Field of Classification Search
CPC ............... A61F 2/2442; A61F 2/2445; A61F 2250/0004; A61F 2220/0016; A61F 2/2439; A61F 2/243; A61F 2/2433; A61F 2002/30537; A61F 2/2466; A61B 17/00234; A61B 17/0644; A61B 2017/00243; A61B 17/068; A61B 2017/00783; A61B 2017/00867; A61B 2017/0647; A61B 2017/0409; A61B 2017/00862; A61B 17/0401; A61B 2017/12018; A61B 2017/0414
USPC ..................... 623/2.11, 2.36, 2.37, 2.38, 2.41
See application file for complete search history.

(56) References Cited

U.S. PATENT DOCUMENTS 4,602,911 A   7/1986 Ahmadi et al.
4,820,299 A   4/1989 Philippe et al.
(Continued)

FOREIGN PATENT DOCUMENTS

CA    2456991       3/2003
CN    101268183 A   9/2008
(Continued)

OTHER PUBLICATIONS

Bonow, et al., "ACC/AHA 2006 Guidelines for the Management of Patients with Valvular Heart Disease," *J. American College of Cardiology* 48(3):1-148 (2006).
(Continued)

*Primary Examiner* — Ashley Fishback
*Assistant Examiner* — Jing Ou
(74) *Attorney, Agent, or Firm* — Knobbe, Martens, Olson & Bear, LLP

(57) ABSTRACT

In general, in an aspect, an annulus of a heart valve is caused to dilate to a predetermined configuration by pushing a delivery tool distally through the annulus from one heart chamber to another heart chamber. A valve support is attached to the delivery tool. The valve support has a plurality of barbs or hooks attached thereon. While the annulus is dilated, the valve support is attached to tissue at locations along the annulus by attaching the barbs or hooks to the tissue. After attachment, the support is caused to contract.

12 Claims, 21 Drawing Sheets

(51) Int. Cl.
*A61B 17/068* (2006.01)
*A61B 17/04* (2006.01)
*A61B 17/12* (2006.01)

(56) References Cited

U.S. PATENT DOCUMENTS

| | | | |
|---|---|---|---|
| 5,254,127 A | 10/1993 | Wholey et al. | |
| 5,674,280 A | 10/1997 | Davidson et al. | 623/2.36 |
| 5,772,590 A | 6/1998 | Webster, Jr. | |
| 5,824,066 A | 10/1998 | Gross | |
| 5,968,053 A * | 10/1999 | Revelas | 606/108 |
| 5,984,959 A | 11/1999 | Robertson et al. | |
| 6,001,127 A | 12/1999 | Schoon et al. | |
| 6,210,432 B1 | 4/2001 | Solem et al. | |
| 6,254,642 B1 | 7/2001 | Taylor | |
| 6,355,030 B1 | 3/2002 | Aldrich et al. | |
| 6,582,460 B1 * | 6/2003 | Cryer | 623/1.11 |
| 6,652,537 B2 | 11/2003 | Mercereau et al. | |
| 6,702,826 B2 | 3/2004 | Liddicoat et al. | |
| 6,726,716 B2 | 4/2004 | Marquez | |
| 6,776,791 B1 | 8/2004 | Stallings et al. | |
| 6,790,231 B2 | 9/2004 | Liddicoat et al. | |
| 6,913,608 B2 | 7/2005 | Liddicoat et al. | |
| 6,942,694 B2 | 9/2005 | Liddicoat et al. | |
| 7,007,698 B2 | 3/2006 | Thornton | |
| 7,063,722 B2 | 6/2006 | Marquez | |
| 7,081,131 B2 | 7/2006 | Thornton | |
| 7,329,280 B2 | 2/2008 | Bolling et al. | |
| 7,357,815 B2 | 4/2008 | Shaoulian et al. | |
| 7,482,936 B2 | 1/2009 | Bolling | |
| 7,556,647 B2 | 7/2009 | Drews et al. | |
| 7,988,725 B2 | 8/2011 | Gross et al. | |
| 8,012,202 B2 | 9/2011 | Alameddine | |
| 8,287,591 B2 | 10/2012 | Keidar et al. | |
| 8,430,926 B2 | 4/2013 | Kirson | |
| 8,551,161 B2 | 10/2013 | Dolan | |
| 8,579,964 B2 | 11/2013 | Lane et al. | |
| 8,784,482 B2 | 7/2014 | Rahdert et al. | |
| 2002/0002401 A1 * | 1/2002 | McGuckin et al. | 623/1.19 |
| 2002/0042621 A1 | 4/2002 | Liddicoat et al. | |
| 2002/0151961 A1 | 10/2002 | Lashinski et al. | |
| 2002/0161377 A1 | 10/2002 | Rabkin | |
| 2002/0173841 A1 | 11/2002 | Ortiz et al. | |
| 2003/0040793 A1 | 2/2003 | Marquez | |
| 2003/0093148 A1 | 5/2003 | Bolling | |
| 2003/0158570 A1 | 8/2003 | Ferrazzi | |
| 2003/0199975 A1 | 10/2003 | Gabbay | |
| 2003/0199987 A1 | 10/2003 | Berg et al. | 623/23.64 |
| 2003/0212453 A1 | 11/2003 | Mathis et al. | |
| 2003/0225420 A1 | 12/2003 | Wardle | |
| 2003/0233142 A1 | 12/2003 | Morales et al. | |
| 2004/0010275 A1 | 1/2004 | Jacobs et al. | |
| 2004/0067544 A1 | 4/2004 | Vogel et al. | |
| 2004/0092965 A1 | 5/2004 | Parihar | |
| 2004/0122516 A1 | 6/2004 | Fogarty et al. | |
| 2004/0127982 A1 * | 7/2004 | Machold et al. | 623/2.36 |
| 2004/0148019 A1 | 7/2004 | Vidlund et al. | |
| 2004/0148020 A1 | 7/2004 | Vidlund et al. | |
| 2004/0167620 A1 * | 8/2004 | Ortiz et al. | 623/2.11 |
| 2004/0172063 A1 | 9/2004 | Li et al. | |
| 2004/0186565 A1 | 9/2004 | Schreck | |
| 2004/0193191 A1 | 9/2004 | Starksen et al. | |
| 2004/0193261 A1 | 9/2004 | Berreklouw | |
| 2004/0236419 A1 | 11/2004 | Milo | |
| 2004/0243104 A1 | 12/2004 | Seddon | |
| 2004/0243227 A1 | 12/2004 | Starksen et al. | |
| 2004/0243230 A1 * | 12/2004 | Navia et al. | 623/2.36 |
| 2004/0249400 A1 | 12/2004 | Vargas et al. | |
| 2004/0249453 A1 | 12/2004 | Cartledge et al. | |
| 2004/0260394 A1 * | 12/2004 | Douk et al. | 623/2.36 |
| 2005/0004665 A1 | 1/2005 | Aklog | |
| 2005/0004668 A1 | 1/2005 | Aklog et al. | |
| 2005/0038508 A1 * | 2/2005 | Gabbay | 623/2.36 |
| 2005/0075713 A1 | 4/2005 | Biancucci et al. | |
| 2005/0080454 A1 | 4/2005 | Drews et al. | |
| 2005/0131533 A1 | 6/2005 | Alfieri et al. | |
| 2005/0137701 A1 | 6/2005 | Salahieh et al. | |
| 2005/0182290 A1 * | 8/2005 | Lau et al. | 600/37 |
| 2005/0182486 A1 * | 8/2005 | Gabbay | 623/2.11 |
| 2005/0192629 A1 | 9/2005 | Saadat et al. | |
| 2005/0267560 A1 | 12/2005 | Bates | |
| 2005/0288776 A1 | 12/2005 | Shaoulian et al. | |
| 2005/0288783 A1 | 12/2005 | Shaoulian et al. | |
| 2006/0025855 A1 | 2/2006 | Lashinski et al. | |
| 2006/0025858 A1 | 2/2006 | Alameddine | |
| 2006/0106305 A1 | 5/2006 | Lau | |
| 2006/0106456 A9 * | 5/2006 | Machold et al. | 623/2.36 |
| 2006/0129235 A1 | 6/2006 | Seguin et al. | |
| 2006/0149349 A1 | 7/2006 | Garbe | |
| 2006/0178733 A1 | 8/2006 | Pinchuk et al. | |
| 2006/0184240 A1 | 8/2006 | Jimenez et al. | |
| 2006/0184241 A1 | 8/2006 | Marquez | |
| 2006/0195012 A1 | 8/2006 | Mortier et al. | |
| 2006/0206203 A1 | 9/2006 | Yang et al. | |
| 2006/0241746 A1 | 10/2006 | Shaoulian et al. | |
| 2006/0241747 A1 | 10/2006 | Shaoulian et al. | |
| 2007/0005129 A1 | 1/2007 | Damm et al. | |
| 2007/0016287 A1 | 1/2007 | Cartledge et al. | |
| 2007/0027533 A1 | 2/2007 | Douk | |
| 2007/0050019 A1 | 3/2007 | Hyde | |
| 2007/0055368 A1 | 3/2007 | Rhee et al. | |
| 2007/0112423 A1 | 5/2007 | Chu | |
| 2007/0112425 A1 | 5/2007 | Schaller et al. | |
| 2007/0142907 A1 * | 6/2007 | Moaddeb et al. | 623/2.11 |
| 2007/0156233 A1 * | 7/2007 | Kapadia et al. | 623/2.11 |
| 2007/0161846 A1 | 7/2007 | Nikolic et al. | |
| 2007/0239272 A1 | 10/2007 | Navia et al. | |
| 2007/0244553 A1 | 10/2007 | Rafiee et al. | |
| 2007/0250161 A1 | 10/2007 | Dolan | |
| 2007/0276478 A1 | 11/2007 | Marmureanu et al. | |
| 2007/0282436 A1 | 12/2007 | Pinchuk | |
| 2007/0293942 A1 | 12/2007 | Mirzaee | |
| 2007/0299543 A1 | 12/2007 | Cartledge et al. | |
| 2008/0027483 A1 | 1/2008 | Cartledge et al. | |
| 2008/0067713 A1 | 3/2008 | Bordener | |
| 2008/0077235 A1 | 3/2008 | Kirson | |
| 2008/0167713 A1 | 7/2008 | Bolling | |
| 2008/0177380 A1 | 7/2008 | Starksen et al. | |
| 2008/0255661 A1 | 10/2008 | Straubinger et al. | |
| 2008/0288060 A1 | 11/2008 | Kaye et al. | |
| 2009/0087414 A1 | 4/2009 | Edelman et al. | |
| 2009/0149872 A1 | 6/2009 | Gross et al. | |
| 2009/0177276 A1 | 7/2009 | Carpentier et al. | |
| 2009/0182419 A1 | 7/2009 | Bolling | |
| 2009/0198316 A1 | 8/2009 | Laske et al. | |
| 2009/0264996 A1 | 10/2009 | Vanermen et al. | |
| 2009/0287299 A1 | 11/2009 | Tabor et al. | |
| 2009/0287304 A1 | 11/2009 | Dahlgren et al. | |
| 2010/0049315 A1 | 2/2010 | Kirson | |
| 2010/0087855 A1 | 4/2010 | Leung et al. | |
| 2010/0121433 A1 | 5/2010 | Bolling | |
| 2010/0152838 A1 | 6/2010 | Kang et al. | |
| 2010/0152840 A1 | 6/2010 | Seguin et al. | |
| 2010/0249920 A1 | 9/2010 | Bolling | |
| 2010/0298929 A1 | 11/2010 | Thornton | |
| 2011/0022166 A1 | 1/2011 | Dahlgren et al. | |
| 2011/0106247 A1 | 5/2011 | Miller et al. | |
| 2011/0202127 A1 | 8/2011 | Mauch et al. | |
| 2011/0224785 A1 | 9/2011 | Hacohen | |
| 2011/0288632 A1 | 11/2011 | White | |
| 2011/0319989 A1 | 12/2011 | Lane et al. | |
| 2012/0027116 A1 | 2/2012 | Etemad | |
| 2012/0053680 A1 | 3/2012 | Bolling et al. | |
| 2012/0109288 A1 | 5/2012 | Bolling | |
| 2012/0109289 A1 | 5/2012 | Bolling | |
| 2012/0308610 A1 | 12/2012 | Edelman et al. | |
| 2013/0123910 A1 | 5/2013 | Cartledge et al. | |
| 2013/0177600 A1 | 7/2013 | Edelman et al. | |
| 2014/0039612 A1 | 2/2014 | Dolan | |
| 2014/0163690 A1 | 6/2014 | White | |
| 2014/0277427 A1 | 9/2014 | Ratz et al. | |
| 2014/0277563 A1 | 9/2014 | White | |

(56) References Cited

U.S. PATENT DOCUMENTS

FOREIGN PATENT DOCUMENTS

| | | | |
|---|---|---|---|
| CN | 101268183 B | 11/2008 | |
| EP | 1874919 B1 | 6/2010 | |
| EP | 2 047 824 | 5/2012 | |
| EP | 2 656 816 | 10/2013 | |
| ES | 2347078 T3 | 10/2010 | |
| JP | H 588612 | 12/1993 | |
| JP | 2002-525169 | 8/2002 | ............... A61F 2/24 |
| JP | 2005-537067 | 12/2005 | |
| JP | 2008-528117 | 7/2008 | ............... A61F 2/84 |
| JP | 2008-534086 | 8/2008 | |
| JP | 2008-538587 A | 10/2008 | |
| JP | 2010-284536 | 12/2010 | |
| JP | 2012-224644 A | 11/2012 | |
| JP | 05174656 B2 | 4/2013 | |
| WO | WO 90/09153 | 8/1990 | |
| WO | WO 93/15690 | 8/1993 | |
| WO | WO 97/12565 | 4/1997 | |
| WO | WO 97/20524 | 6/1997 | |
| WO | WO 98/24386 | 6/1998 | |
| WO | WO 99/29269 | 6/1999 | |
| WO | WO 99/49816 | 10/1999 | |
| WO | WO 00/07521 | 2/2000 | |
| WO | WO 00/18333 | 4/2000 | ............... A61F 2/24 |
| WO | WO 00/44311 | 8/2000 | |
| WO | WO 00/62715 | 10/2000 | |
| WO | WO 01/89440 A2 | 11/2001 | |
| WO | WO 01/89440 A3 | 11/2001 | |
| WO | WO 02/094132 | 11/2002 | ............... A61F 2/00 |
| WO | WO 03/017874 | 3/2003 | |
| WO | WO 03/053289 | 7/2003 | ............... A61F 2/24 |
| WO | WO 03/080150 | 10/2003 | |
| WO | WO 03/105670 | 12/2003 | |
| WO | WO 03/105730 | 12/2003 | |
| WO | WO 2004/014282 | 2/2004 | |
| WO | WO 2004/019816 | 3/2004 | |
| WO | WO 2004/019826 | 3/2004 | ............... A61F 2/24 |
| WO | WO 2004/030569 A2 | 4/2004 | |
| WO | WO 2004/030569 A3 | 4/2004 | |
| WO | WO 2004/031717 | 4/2004 | |
| WO | WO 2004/032717 | 4/2004 | |
| WO | WO 2004/103223 | 12/2004 | |
| WO | WO 2004/112657 A1 | 12/2004 | |
| WO | WO 2005/002424 A2 | 1/2005 | |
| WO | WO 2005/002424 A3 | 1/2005 | |
| WO | WO 2005/007037 | 1/2005 | |
| WO | WO 2005/046488 | 5/2005 | |
| WO | WO 2006/052687 | 5/2006 | ............ A61F 17/064 |
| WO | WO 2006/086135 | 8/2006 | ............... A61F 2/06 |
| WO | WO 2006/086434 | 8/2006 | |
| WO | WO 2006/105084 | 10/2006 | |
| WO | WO 2006/116129 A2 | 11/2006 | |
| WO | WO 2006/116357 A1 | 11/2006 | |
| WO | WO 2007/021834 | 2/2007 | |
| WO | WO 2008/088716 | 7/2008 | |
| WO | WO 2009/140268 A1 | 11/2009 | |
| WO | WO 2012/027116 | 3/2012 | |

OTHER PUBLICATIONS

Braunberger et al., "Very Long-Tenn Results (More Than 20 years) of Valve Repair with Carpentier's Techniques in Nonrheumatic Mitral Valve Insufficiency," *Circulation*, 104:I8-I11 (2001).

Braunwald et al., "Conservative Management of tricuspid Regurgitation in Patients Undergoing Mitral Valve Replacement," *Circulation*, XXXV and XXXVI:I63-I69 (1967).

Carpentier et al., "Surgical Management of Acquired Tricuspid Valve Disease," *J. Thoracic and Cardiovascular Surgery*, 67(1):53-65 (1974).

Center for Devices and Radiological Health, U.S. Dept. of Health and Human Services Food and Drug Administration "Guidance for Annuloplasty Rings 510(k) Submissions; Final Guidance for Industry and FDA Staff ," 1-15 (2001).

Cosgrove et al., Mitral Valvuloplasty, *Curr. Probl. Cardiol.*, 359-405 (1989).

Dreyfus et al., "Secondary Tricuspid Regurgitation or Dilatation : Which Should Be the Criteria for Surgical Repair ?," *Ann. Thorac. Surg.*, 79:127-32 (2005).

Leung et al., "Barbed, Bi-directional Surgical Sutures : In Vivo Strength and Histopathology Evaluations," *Society for Biomaterials $28^{th}$ Annual Meeting Transactions*, #724 (2003).

Magovern et al., "Sutureless Artificial Heart Valves," *Circulation*, 27:784-788 (1963).

McCarthy et al., "Tricuspid Valve Repair: Durability and Risk Factors for Failure," *J. Thoracic and Cardiovascular Surgery*, 127:674-85 (2004).

Nath et al., "Impact of Tricuspid Regurgitation on Long-Term Survival," *J. American College of Cardiology*, 43(3):405-409 (2004).

Navia et al., "Surgical Management of Secondary Tricuspid Valve Regurgitation : Anulus, Commissure, or Leaflet Procedure ?," Abstract presented at *American Association for Thoracic Surgery Annual Meeting* (2009).

Rogers et al., "The Tricuspid Valve : Current Perspective and Evolving Management of Tricuspid Regurgitation," *Circulation*, 119:2718-2725 (2009).

Sagie et al., "Determinants of Functional Tricuspid Regurgitation in Incomplete Tricuspid Valve Closure: Doppler Color Flow Study of 109 Patients," *J. American College of Cardiology*, 24:446-53 (1994).

Savage et al., "Use of Mitral Valve Repair : Analysis of Contemporary United States Experience Reported to the Society of Thoracic Surgeons National Cardiac Database," *Ann. Thorac Surg.*, 75:820-825 (2003).

Shiran et al., "Tricuspid Regurgitation in Mitral Valve Disease," *J. American College of Cardiology*, 53(5):401-408 (2009).

Song et al., "Factors Associated with Development of Late Significant Tricuspid Regurgitation after Successful Left-Sided Valve Surgery," *Heart*, 95:931-936 (2009).

Tang et al., "Tricuspid Valve Repair with an Annuloplasty Ring Results in Improved Long-Term Outcomes," *Circulation*, 114:1577-1581 (2006).

Thompson, "Percutaneous Heart Valve Technology: The Mitral Challenge," *Medtech Insight*, 11(2):38-52 (2009).

Zlotnick et al., "A Perfectly Functioning Magovern-Cromie Sutureless Prosthetic Aortic Valve 42 Years After Implantation," *Circulation*, 117:e1-e2 (2008).

International Preliminary Report on Patentability for App. Ser. No. PCT/US08/050224, dated Jul. 14, 2009 (9 pages).

U.S. Appl. No. 12/407,656, filed Mar. 19, 2009; Pending claims; and Transaction History.

International Search Report, Patent Cooperation Treaty, dated Jul. 1, 2008 (13 pages).

International Search Report and Written Opinion for App. Ser. No. PCT/US2010/027943, dated Jul. 13, 2010, 16 pages.

European Search Report; Application No. 11186500.2-1659; pp. 5, Sep. 20, 2013.

European Search Report; Application No. 08727364.5-1651; pp. 3, Oct. 8, 2013.

European Office Action; Application No. 11186500.2-1659; pp. 6, Oct. 11, 2013.

B. Braun Medical Inc., Pulmonary Embolism: IVC Filters. Retrieved from the Internet: http://www.bbraunusa.com/pe/pe05a.html [retrieved on Dec. 14, 2006], 4 pages.

Boston Scientific, Device Details. Retrieved from the Internet: http://bostonscientific.com/med_specialty/deviceDetail.jsp [retrieved on Aug. 31, 2006], 1 page.

Google Images, Recurved Hooks. Retrieved from the Internet: www.implementology.org.pf and personal.cityu.edu.hk [retrieved on Dec. 14, 2006], 1 page.

Transaction History for U.S. Appl. No. 12/407,656, filed Mar. 19, 2009.

Transaction History for U.S. Appl. No. 13/347,051, filed Jan. 10, 2012.

Transaction History for U.S. Appl. No. 13/347,052, filed Jan. 10, 2012.

Transaction History for U.S. Appl. No. 12/563,293, filed Sep. 21, 2009.

(56) References Cited

OTHER PUBLICATIONS

Transaction History for U.S. Appl. No. 12/794,235, filed Jun. 4, 2010.
Transaction History for U.S. Appl. No. 12/868,624, filed Aug. 25, 2010.
Office Action from Japanese App. Ser. No. 2009-544986, dated Aug. 13, 2012, 6 pages.
International Search Report and Written Opinion for App. Ser. No. PCT/US2011/039022, dated Sep. 22, 2011, 11 pages.
Application and Transaction History for U.S. Appl. No. 12/868,624, filed Aug. 25, 2010.
Japanese Office Action with English translation; Application No. 2012-500990; pp. 8, Jan. 8, 2014.
International Preliminary Report on Patentability for App. Ser. No. PCT/US2010/027943, dated Sep. 20, 2011, 12 pages.
International Search Report and Written Opinion for App. Ser. No. PCT/US2011/047345, dated Dec. 7, 2011, 15 pages.
Pending claims for U.S. Appl. No. 13/347,051, filed Jan. 10, 2012.
Pending claims for U.S. Appl. No. 13/347,052, filed Jan. 10, 2012.
Pending claims and Transaction History for U.S. Appl. No. 12/407,656, filed Mar. 19, 2009.
European Office Action; Application No. 08727364.5-1651 pp. 6, Jan. 2, 2014.
U.S. Appl. No. 11/620,955, filed Jan. 8, 2007.
U.S. Appl. No. 12/563,293, filed Sep. 21, 2009.
U.S. Appl. No. 12/794,235, filed Jun. 4, 2010.
European Search Report; Application No. 10754160.9-1659 / 2408400; pp. 6 dated May 3, 2013.
International Preliminary Report on Patentability for App. Ser. No. PCT/US08/050224, dated Jul. 14, 2009, 9 pages.
International Preliminary Report on Patentability; PCT/US2011/047345; pp. 9, dated Feb. 26, 2013.
International Search Report for App. Ser. No. PCT/US08/050224, dated Jul. 1, 2008 (3 pages).
International Search Report and Written Opinion for International Application No. PCT/US2014/026333 dated Jul. 21, 2014.
Japanese Office Action with English translation; Application No. 2012-500990; pp. 8 dated Jan. 8, 2014.
Partial European Search Report; Application No. 11186500.2-1659 / 2412316; pp. 7, dated Jun. 5, 2013.

\* cited by examiner

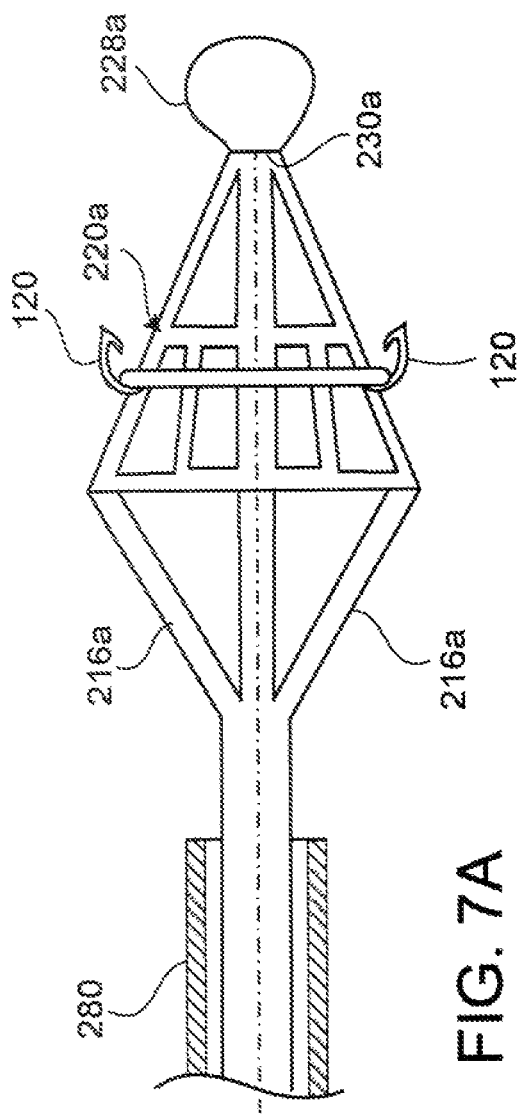
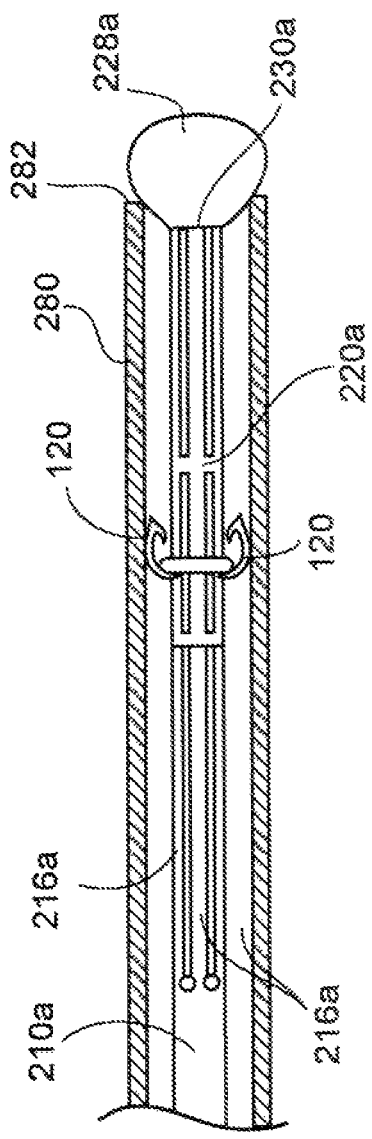
FIG. 7A
FIG. 7B

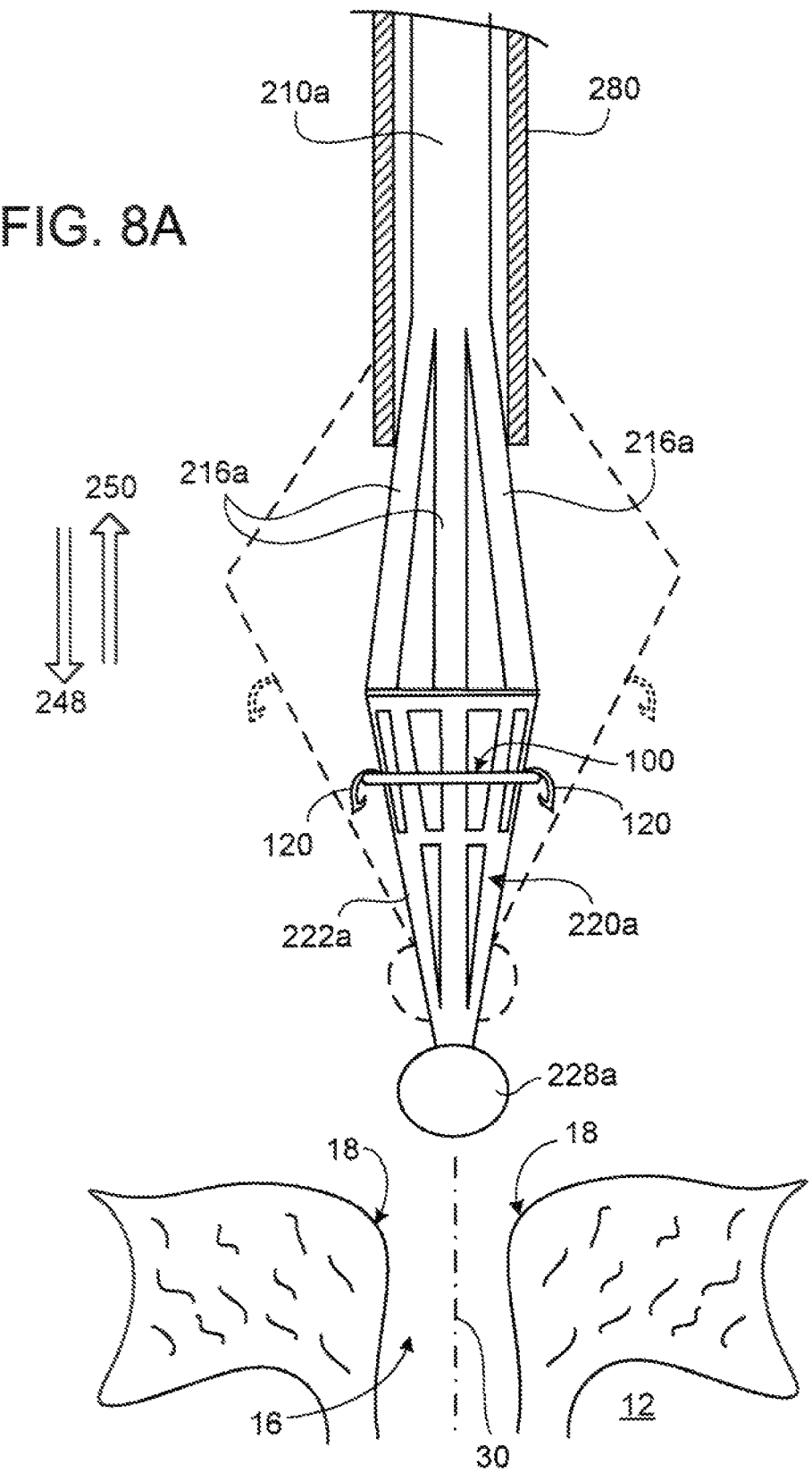

DEVICE FOR TRANSLUMENAL RESHAPING OF A MITRAL VALVE ANNULUS

BACKGROUND

This description relates to reconfiguring heart features.

For example, the annulus of a heart valve, a fibrous ring attached to the wall of the heart, maintains the shape of the valve opening and supports the valve leaflets. In a healthy heart, the annulus is typically round and has a diameter that enables the leaflets to close the valve tightly without flapping during contraction of the heart. Because the annulus of the tricuspid valve, for example, is supported more stably by the heart tissue on one side of the annulus than on the other side, the size and shape of the annulus may become distorted over time. The distortion may prevent the valve from closing properly, allowing blood to regurgitate backwards through the valve. The distortion can be corrected, for example, during open heart surgery, by attaching a ring or other support around the annulus to restore its shape and size.

SUMMARY

In general, in an aspect, a force is applied to a tool toward an annulus of a heart valve to cause the annulus to dilate. While the annulus is dilated, a valve support is attached to tissue at locations along the annulus. After attachment, the support is caused to contract.

Implementations may include one or more of the following features. The valve support is attached to the tool before the annulus is dilated. The valve support is caused to conform to a delivery configuration for attachment. The valve support is expanded before being attached to the tool. The valve support is attached to the tissue by applying a force to the tool in the direction axial to the annulus. The valve support is attached to the tool before attaching the valve support to the tissue. The valve support is attached to the tool by one or more breakable connections, for example, sutures or fingers. The valve support is attached to the tool by forcing the valve support to engage retaining elements on the tool. The valve support is anchored using one or more hooks. The force causes a tapered surface of the tool to engage the annulus. The support is contracted by retracting the tapered head from the annulus. The support contracts itself.

In general, in an aspect, an annulus of a heart valve is caused to dilate to a predetermined configuration. While the annulus is dilated, a valve support is attached to tissue at locations along the annulus. After attachment, the support is caused to contract.

Implementations may include one or more of the following features. The valve support is expanded to a delivery configuration before the valve support is attached to the tissue. The valve support is displaced axially along a tapered head of a delivery tool to expand it. The valve support is releasably attached to the tapered head. The annulus of the heart valve is dilated by forcing the tapered head of the delivery tool into the heart valve in a direction axial to the annulus. The support is contracted by retracting the tapered head from the heart valve. The valve support is released when the tapered head is retracted by breaking a connection between the valve support and the tapered head of the tool. The valve support is attached to tissue by forcing hooks into the tissue.

In general, in an aspect, a valve support is pushed towards an annulus of a heart valve to cause hooks of the support to be driven into tissue at locations along the annulus. The hooks are more securely embedded in the tissue by pulling on the support.

Implementations may include one or more of the following features. The valve support includes an annular body, and the hooks rotate about the annular body to become more securely embedded. The valve support is pushed by pushing on a delivery tool that carries the valve support. The support is pulled by pulling on a delivery tool that carries the support. The valve support is released from the tool after the hooks are more securely embedded.

In general, in an aspect, a catheter traverses a body lumen to place a delivery tool that carries a valve support at an annulus of a heart valve. The catheter is pushed toward the annulus of the heart valve to cause the delivery tool to dilate the annulus.

Implementations may include one or more of the following features. The catheter is pushed toward the annulus to attach the valve support to the annulus. The catheter is pulled to release the valve support after it is attached to the annulus. The valve support then contracts. The valve support is sheathed before the catheter is caused to traverse the body lumen and unsheathed in the vicinity of the heart valve. The sheathing and unsheathing is done by moving the catheter and the sheath relative to one another to cause the valve support to be compressed and expanded, respectively.

In general, in an aspect, an apparatus includes an annular heart valve support and hooks connected to the support to attach the support along an annulus of a heart valve, each of the hooks having (a) a sharp free end facing a first direction, (b) a connection end where the hook is attached to the support, and (c) a bend located between the free end and the connection end, the bend defining a sharp feature facing in a second direction generally opposite to the first direction.

Implementations may include one or more of the following features. The support is expandable and contractable. The support includes at least one of stainless steel, gold, Nitinol, and a biologically compatible elastomer. The support includes a helical torsion spring. The hooks are rotatable about the support. The hooks comprise at least one of platinum, gold, palladium, rhenium, tantalum, tungsten, molybdenum, nickel, cobalt, stainless steel, Nitinol, and alloys thereof.

In general, in an aspect, an apparatus includes a tool bearing a tapered outer surface, a heart valve support, and a connection between the tool and the support to translate forces from the tool to the support in each of two opposite directions along an axis of a heart valve and to release when the force along one of the axial directions exceeds a predetermined threshold.

Implementations may include one or more of the following features. The tool includes a tapered outer surface. The tapered outer surface includes interconnected struts defining apertures. The connection includes at least one retaining element on an outer surface of the tool. The valve support includes hooks each having a sharp free end facing in a first direction, a connection end where the hook is attached to the support, and a bend located between the free end and the connection end, the bend defining a sharp feature facing in a second direction generally opposite the first direction. The tool includes a tip at a narrow end of the tapered outer surface, and the tapered outer surface is evertable when the tip is pulled toward a broader end of the tapered outer surface. A movable element is connected to the tip and configured to pull the tip to evert the tapered outer surface. A sheath covers the tapered outer surface and cause the tapered outer surface to be collapsed when covered. The tool includes a self-expanding, semi-rigid net.

In general, in an aspect, a force is applied on a tool toward an annular feature of a heart to cause the feature to dilate.

While the feature is dilated, a support is attached to tissue at locations along a periphery of the annular feature. After attachment, the support is caused to contract to reconfigure the feature. In some implementations, the feature comprises a left atrial appendage.

Among advantages of these and other aspects and features are one or more of the following. The heart valve support can be attached simultaneously at multiple locations along the circumference of the valve annular, which reduces the duration and risk of the procedure. In some uses, the valve support can be attached without the physician having a clear view (or any view) of the valve opening, for example, during open heart surgery or when the valve support is delivered on a catheter. The valve support is self-centering and the delivery tool accommodates heart valves and heart valve supports of different sizes. The tool permits blood to flow through the valve while the support is being attached to the valve annulus. Tricuspid valve and mitral valve regurgitation can be reduced.

These and other aspects and features, and combinations of them, may be expressed as apparatus, methods, systems, and in other ways.

Other features and advantages will be apparent from the description and the claims.

DESCRIPTION

FIGS. 7A through 8I show delivery of a heart valve support.

Figure 1A:
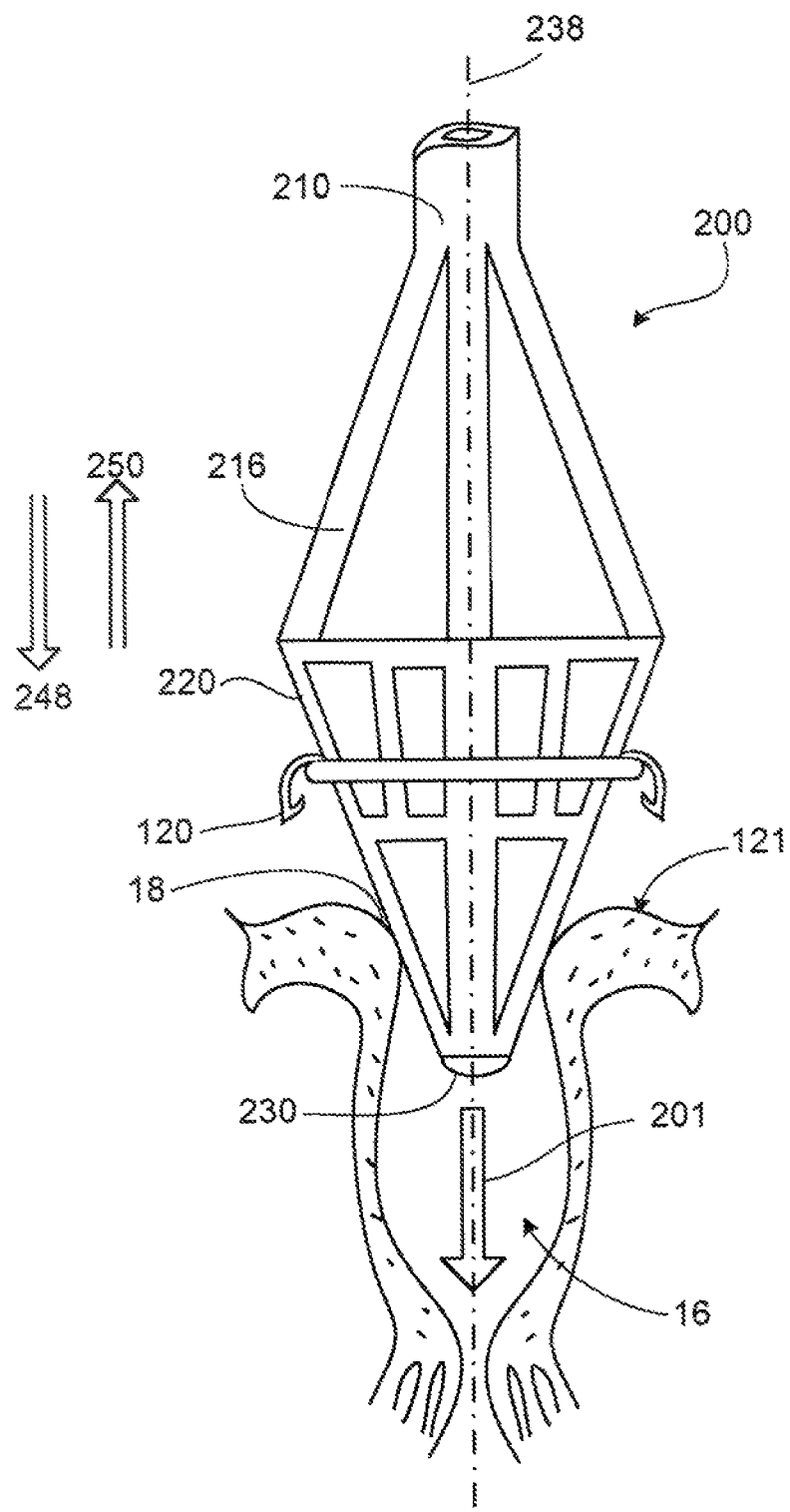
FIGS. 1A through 1H show delivery of a heart valve support.
Figure 1B:
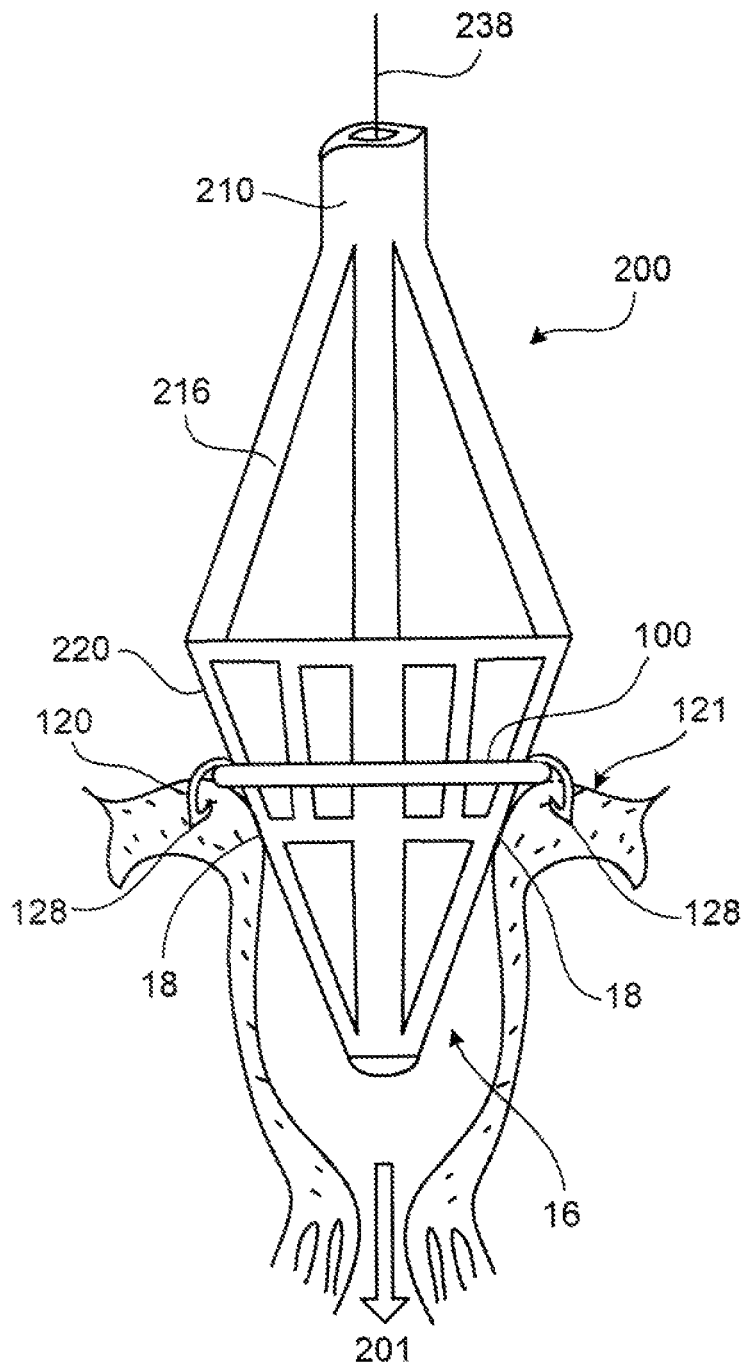
Figure 1C:
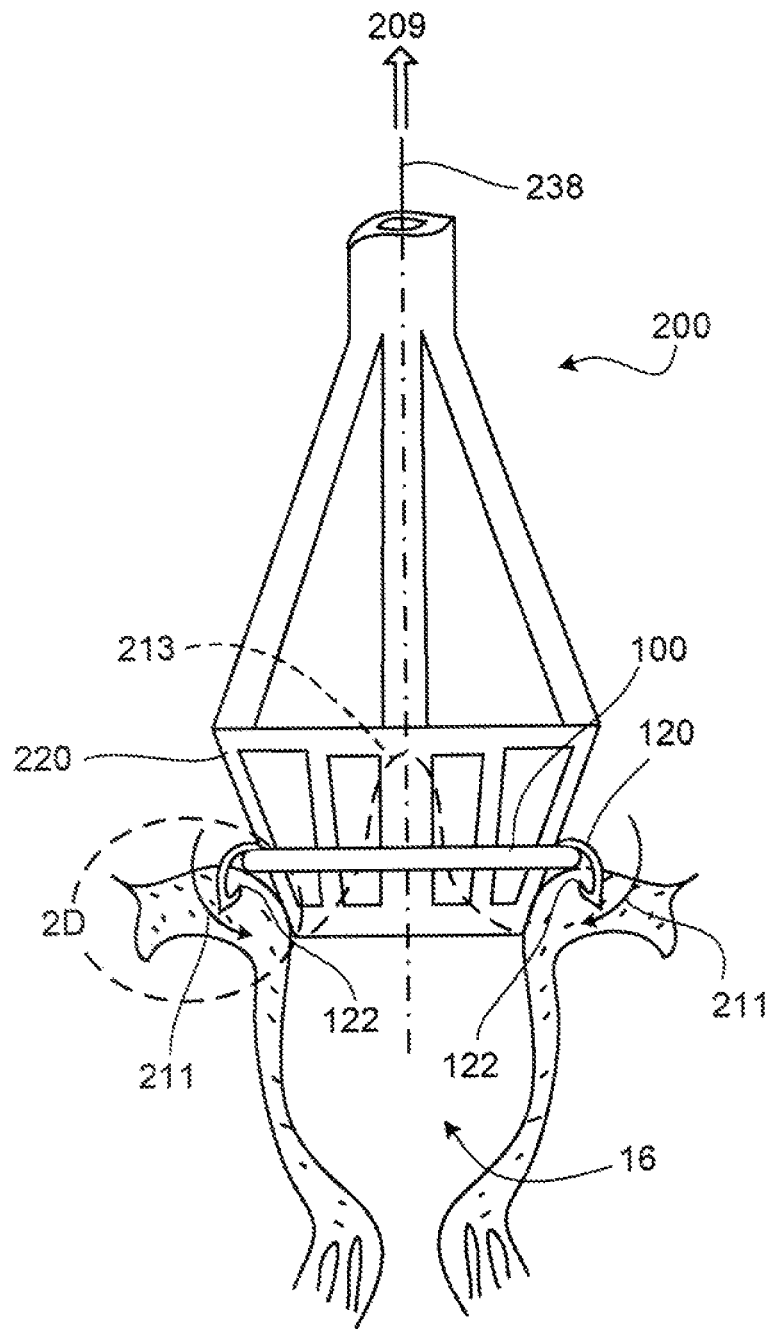
Figure 1D:
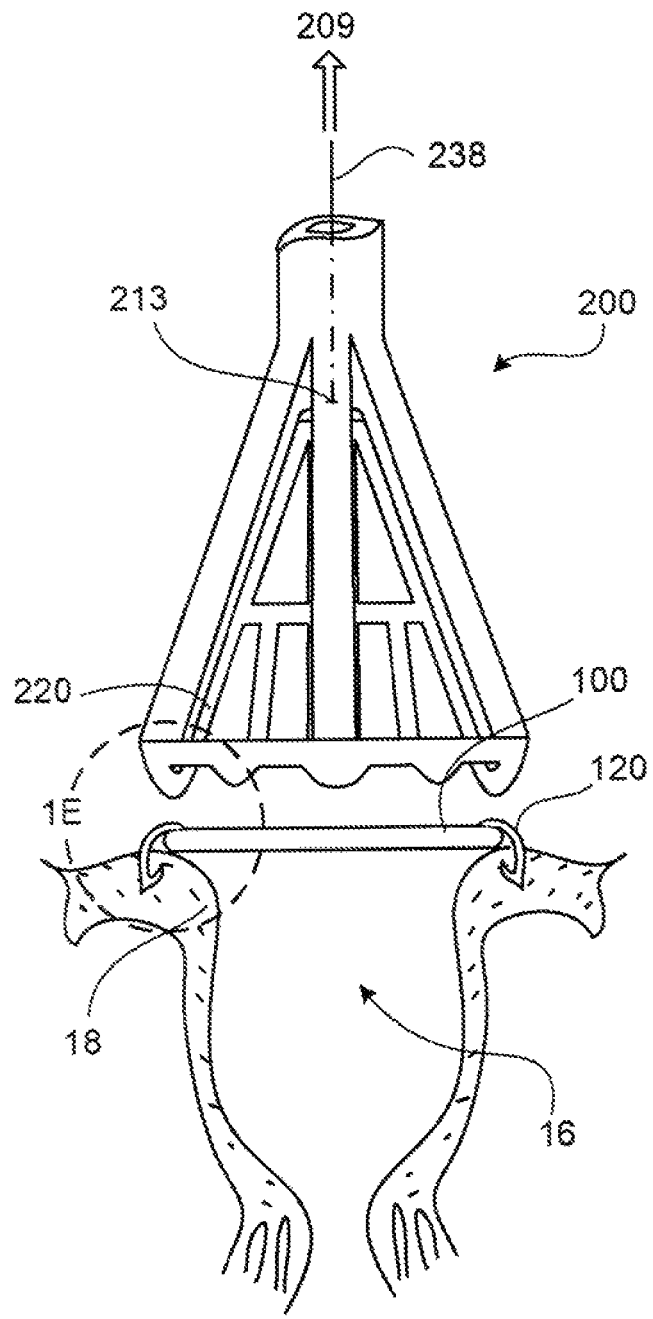
Figure 1E:
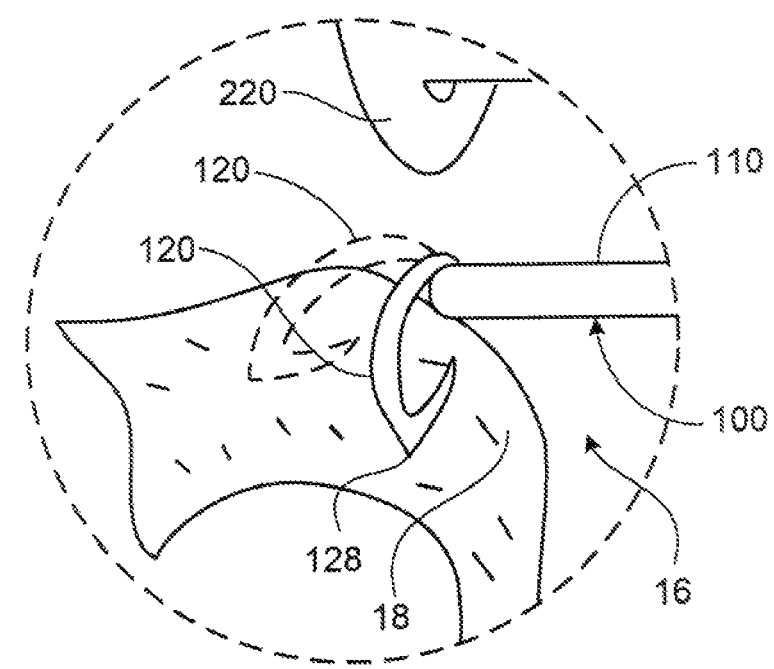
Figure 1F:
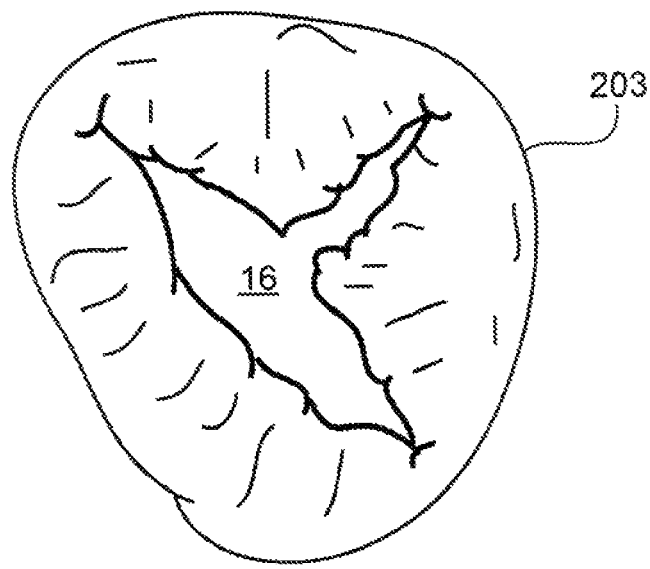
Figure 1G:
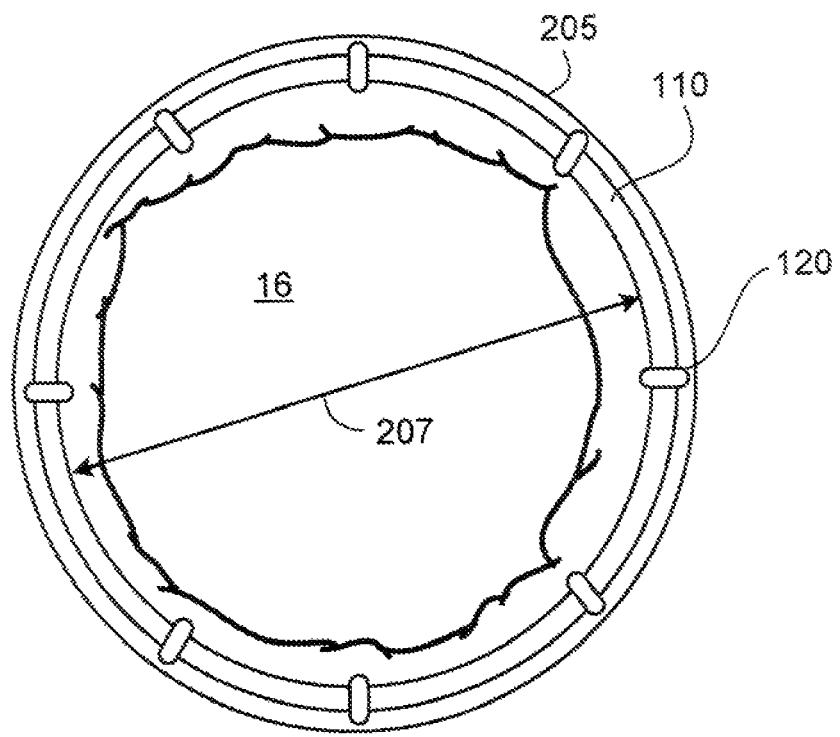
Figure 1H:
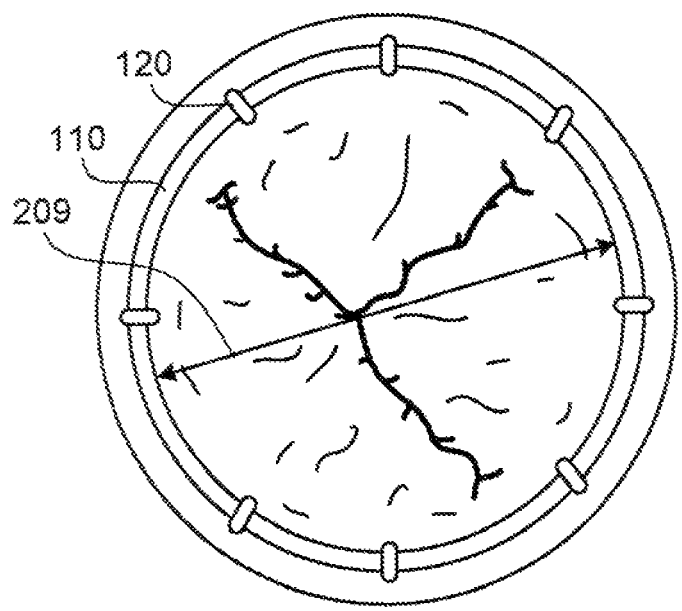

As shown in the examples of FIGS. 1A through 1G distortion of an annulus 18 of a heart valve 16 can be corrected simply and quickly by the following steps:

A. Push 201 (FIG. 1A) a conical head end basket 220 of a delivery tool 200 into the valve to force the distorted annulus (203, FIG. 1F) to conform to a desired configuration (e.g., a circle 205, FIG. 1G) and to a size that is larger (e.g., in diameter 207) than a desired final diameter 209 of the annulus (FIG. 1H). (The tool and basket are shown in side view and the valve and annulus are shown in sectional side view.)

B. Continue to push 201 the delivery tool to drive an expander heart valve support 100 (which has the desired configuration and the larger size and is temporarily held in its expanded configuration on the tool) towards the annulus to seat multiple recurved hooks 120 located along the periphery of the support simultaneously into the valve tissue at multiple locations along the periphery 121 of the annulus (FIG. 1B).

C. After the hooks are seated, pull 209 (FIG. 1C) on and evert the tip 230 of the head end basket from the inside to cause the support to roll so that the tips 122 of the hooks rotate 211 and embed themselves more securely into the annulus tissue (FIG. 1C).

D. After the hooks are further embedded, continue to pull 209 (FIG. 1D) on the inside 213 of the tip of the head end basket to break the tool away from the support (FIG. 1E), allowing the support to contract to its final size and shape 215 (FIG. 1H) and leaving the support permanently in place to maintain the annulus in the desired final configuration and size.

The entire procedure can be performed in less than a minute in many cases. By temporarily forcing the annulus of the valve to expand to the desired circular shape, it is possible to attach the support quickly, easily, and somewhat automatically by forcing multiple hooks into the tissue at one time. The physician avoids having to attach individual sutures or clips one at a time along the periphery of a distorted annulus and then cinch them together to reform the supported annulus to a desired shape and size. Thus, the physician does not even need to be able to see the annulus clearly (or at all). Once attached, when the tool is removed, the support automatically springs back to its final shape and size.

Figure 2E:
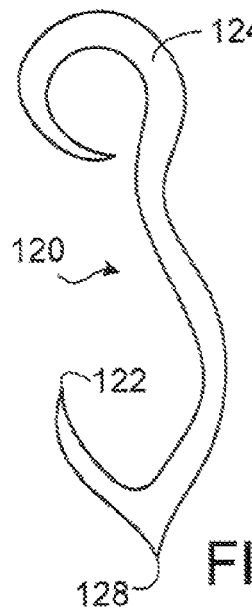
FIG. 2E is a plan view of a recurved hook.
Figure 2A:
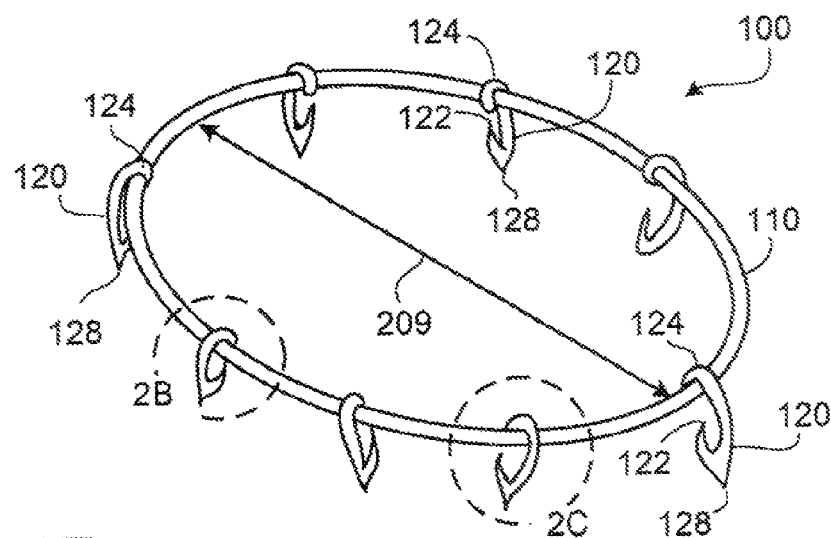
FIGS. 2A through 2D are perspective view of a heart valve support.
Figure 2B:
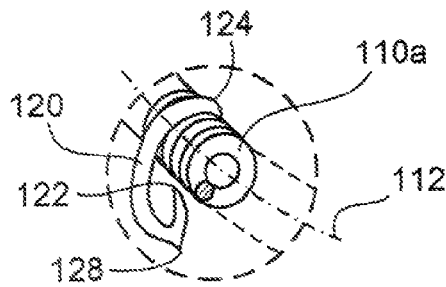
Figure 2C:
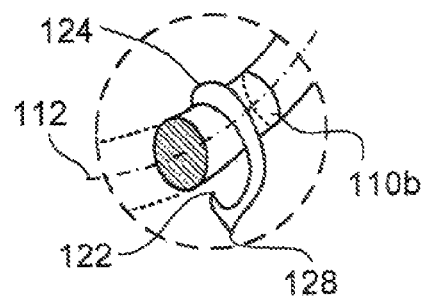
Figure 2D:
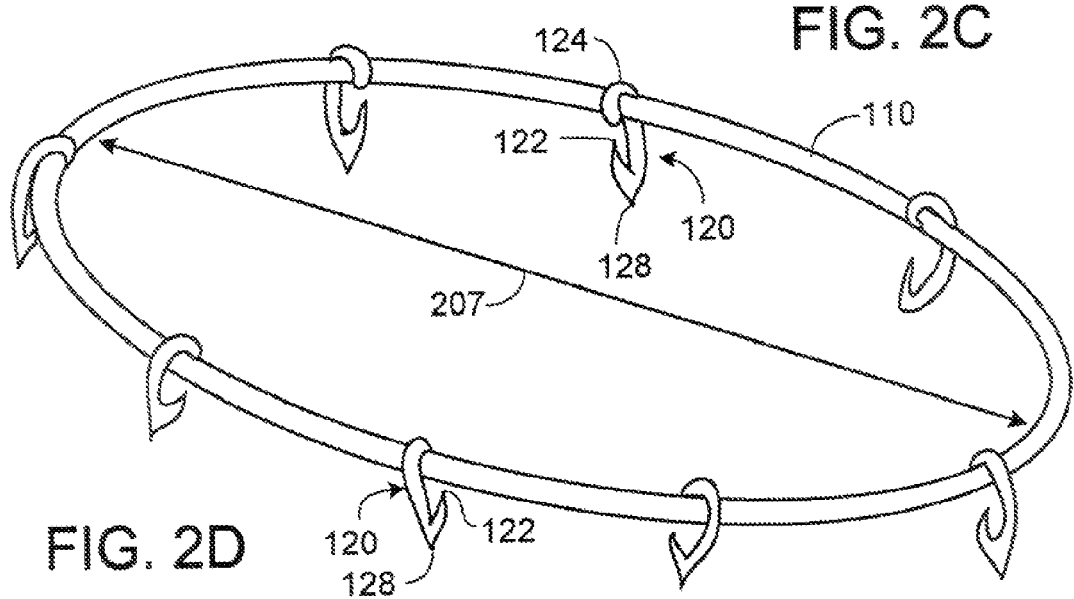

As shown in FIGS. 2A and 2D, in some implementations, the support includes a circular ring body 110 that bears the hooks 120. The body 110 can be expanded from (a) a minimal-diameter long-term configuration (FIG. 2A) to which it conforms after it has been attached to the annulus to (b) an expanded delivery configuration (FIG. 2D) to which it conforms when it is held on the head end basket of the tool and while it is being attached in the steps shown in FIGS. 1A, 1B, and 1C. The long-term configuration is normally circular and has the diameter of a healthy annulus for a particular patient. When attached, the support maintains the health configuration of the annulus so that the valve will work properly.

In some examples, the body 110 has the same shape (e.g., circular) but different diameters in the delivery configuration and the long-term configuration. The body is constructed of a material or in a manner that biases the body to contract to the long-term configuration. For example, all or portions of the body 110 may be formed as a helical spring 110a such as a continuous helical spring connected at opposite ends to form a circular body or one or more interconnected helical spring segments (FIG. 2B). In some examples, the support body 110b may be a band of shape memory material such as Nitinol or a biologically compatible elastomer that will return to the long-term configuration after being expanded to the delivery configuration (FIG. 2C).

The hooks 120 may number as few as three or as many as ten or twenty or more and may be arranged at equal intervals along the body or at unequal intervals as needed to make the body easy and quick to delivery, permanent in its placement, and effective in correcting distortion of the valve annulus. The hooks are configured and together mounted along the circular outer periphery so that they can be inserted simultaneously into the tissue along the periphery of the annulus and then firmly embedded when the tool is pulled away and the basket is everted.

For this reason, as shown in FIG. 2E each of the hooks has two pointed features. One pointed feature is a sharp free end 122 pointing away from the valve leaflets during delivery. The other pointed feature is a barb 128 formed at a bend between the sharp free end 122 and an opposite connection end 124 where the hook is attached, e.g., welded or glued, to the body 110. The barb points toward the valve leaflets during delivery.

Each hook 120 can be formed of biologically compatible materials such as platinum, gold, palladium, rhenium, tantalum, tungsten, molybdenum, nickel, cobalt, stainless steel, Nitinol, and alloys, polymers, or other materials. During delivery the barbs of the hooks are together forced into the tissue at a series of locations around the outer periphery of the temporarily expanded annulus. In a later step, the sharp free ends are forced to rotate somewhat away from the leaflets for permanent attachment.

Figure 3:
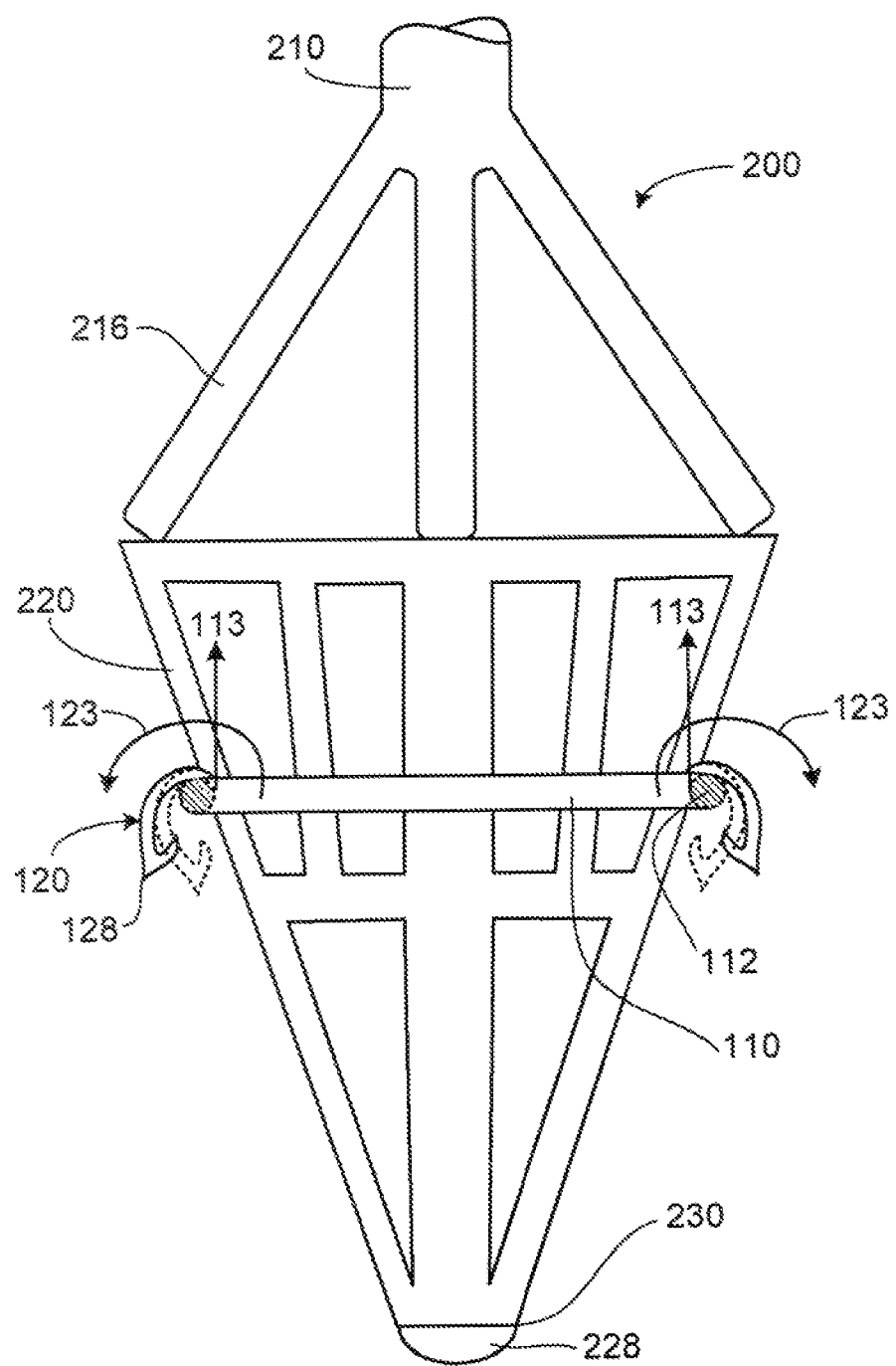
FIG. 3 is a section side view of a heart valve support.

To cause the hooks to rotate during delivery, the hooks 120 are attached permanently to the support body 110 and the support body can be rolled 123 (FIG. 3) about an axis 112 of the support body, as indicated. One way to cause the rolling of the support body and the associated rotation of the hooks is to enable the body to change its configuration by rotation of the entire body about an axis represented by the central circular axis 153, much as a rubber o-ring can be rolled about its central circular axis. The reconfiguration of the body to cause the rotation of the hooks can be achieved in other ways.

In some examples, applying an axial force (arrows 113) to the inner peripheral edge of the ring (we sometimes refer to the support broadly as a ring) will cause the ring to tend to roll and the hooks to embed themselves in the annulus as intended. By properly mounting the inner periphery of the ring on the outer periphery of the delivery tool, the axial force 113 can be applied by pulling the tool away from the leaflets of the valve, as explained earlier.

Figure 4A:
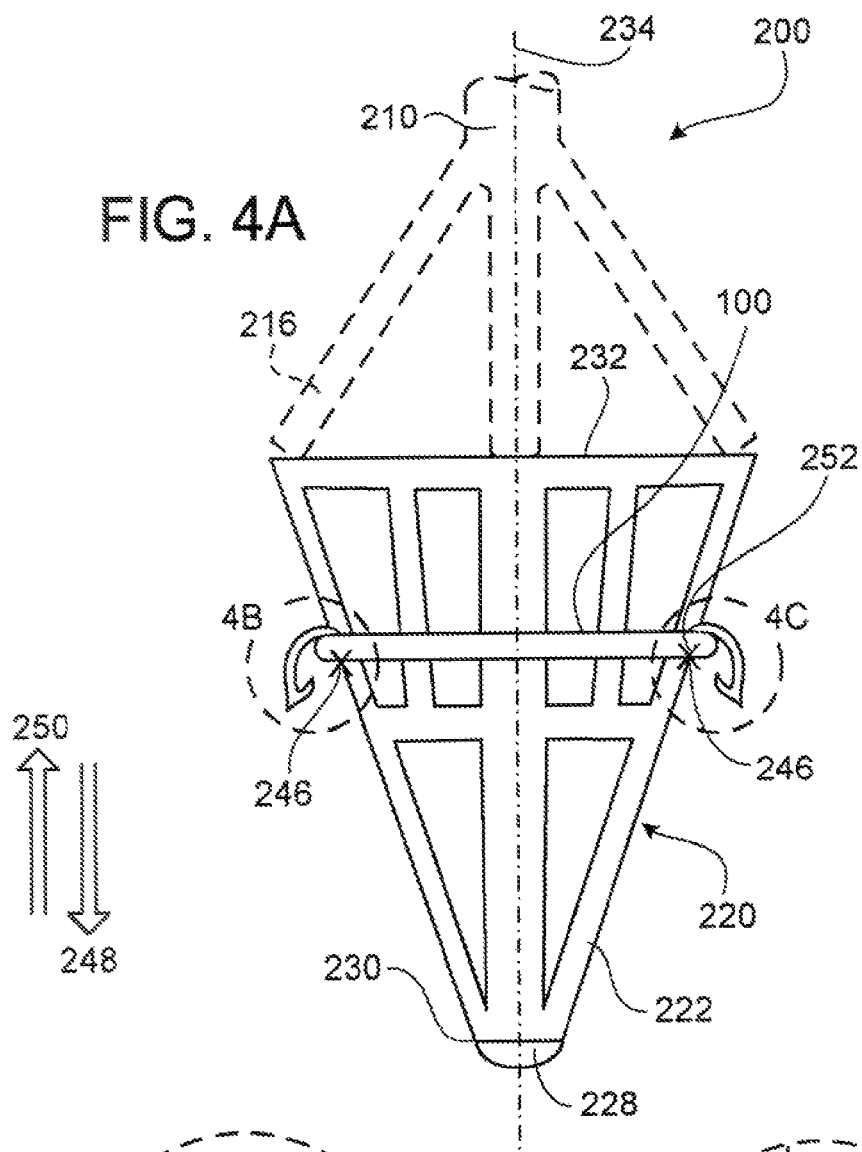
FIGS. 4A through 4C are side and detailed views of a delivery tool and heart valve support.

For delivery to the valve annulus, the valve support 100 is expanded to its delivery configuration and temporarily mounted on a delivery head 220 of the tool 200 (FIG. 4A). The support must be expanded enough in its temporary mounting on the tool so that when the head-end basket of the tool is pushed against the annulus to force it to expand to the size and shape of the expanded support, the annulus has reached a circular, non-distorted shape. The tapered profile of the head end basket of the delivery tool allows the tool to accommodate supports of various sizes.

The heart valve support 100 is held in place on the delivery head 220 using one or more releasable connections 246. The connections 246 are arranged to translate forces from the tool 200 to the support 100 in either of two opposite directions, 248 and 250 toward or away from the leaflets of the valve. When the support has been embedded in the annulus and the tool is pulled in the direction 250 to release it from the support, the force on the connections 246 exceeds a predetermined threshold, the connections break, releasing the tool from the support at the end of the delivery process. The connections 246 may be, in some examples, breakable sutures 252 (FIG. 4A).

Figure 4B:
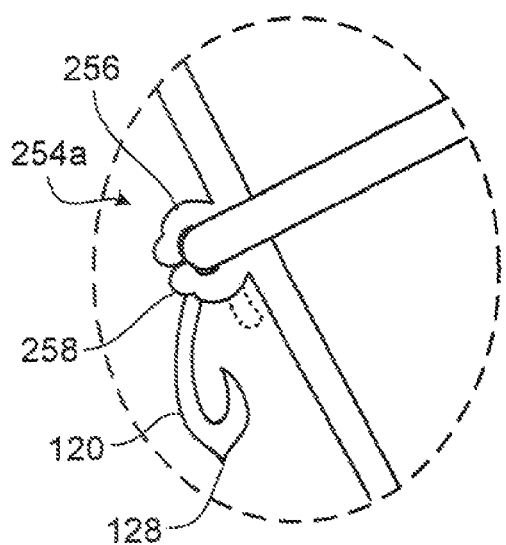
Figure 4C:
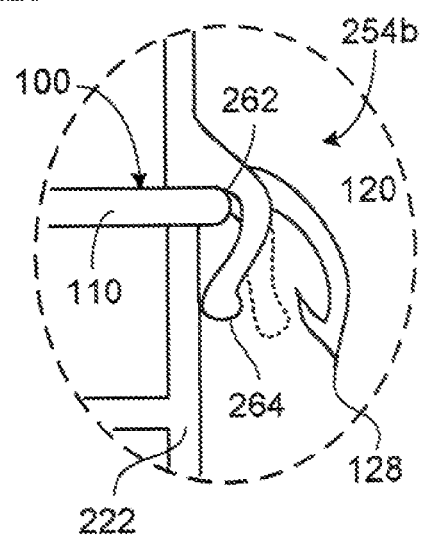

In some examples, the connections 246 include retainers that can take, e.g., the configurations shown as 254a or 254b (FIGS. 4B & 4C, respectively). In the example shown in FIG. 4B, the retaining element 254a has one rigid finger 256 to translate forces from the tool 200 to the support 100 when the tool is moved in direction 248 while the support is attached to the tool and being pushed into the heart tissue. A second deformable finger 258 aids in maintaining the connection between the support 100 and the tool 200 when the tool is moved in direction 250 and is deformable (dashed lines) to release the valve support 100 from the tool 200 when the force in direction 250 relative to the embedded support exceeds a predetermined threshold.

In the example shown in FIG. 4C, the retaining element 254b includes a finger 260 having a crook 262 to receive the support 100 and to translate forces from the tool 200 to the support 100 when the tool is moved in direction 248. The finger has a resiliently deformable tip 264 that is biased towards the tapered body 222 and helps to maintain the connection between the support 100 and the tool 200 and is deformable (shown in hidden lines) to release the valve support 100 from the tool 200 when the tool is moved in the second axial direction 250 against an embedded support and the force exceeds a predetermined threshold.

Figure 5:
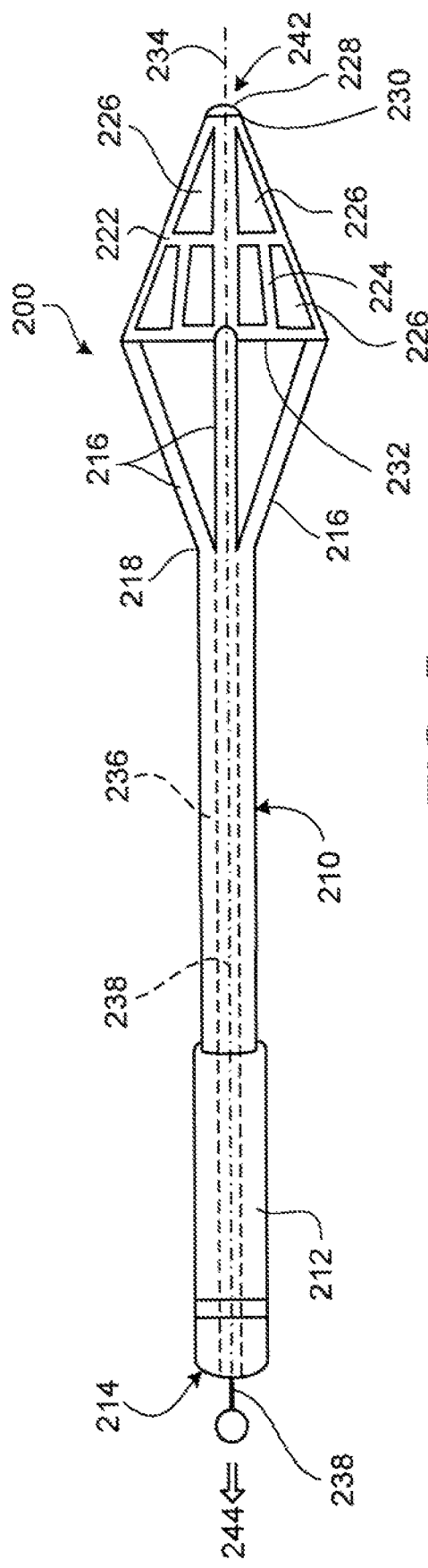
FIG. 5 is a side view of a delivery tool.

As shown in FIG. 5, in an example of a tool 200 that can be used for delivery of the support during open heart surgery, a basket 220 is connected at its broad end to a set of stiff wires or other rigid projections 216 from a long shaft 210 having a handle 212 at the operator's end 214. Thus the projections 216 connect the shaft 210 to the basket 220 and transfer pulling or pushing force between the shaft and the basket (and in turn to the support).

The example of the basket shown in FIG. 5 includes a tapered body 222 having a network of interconnected struts 224 defining an array of openings 226 together forming a tapered semi-rigid net. The basket (which we also sometimes refer to as a delivery head) 220 has a rounded tip 228. The head 222 tapers radially outwardly with distance along a longitudinal axis 234 of the head 220 from the tip 228 towards the operator. The broad end 232 of the tapered body 222 is firmly attached to the projections 216, which taper in the opposite direction from the taper of the basket.

In some implementations, the shaft 210 defines a lumen 236 extending between the heart valve end 218 of the shaft 210 and the handle 212. A wire 238 is arranged to move freely back and forth within the lumen 236. The wire 238 has one end 240 that extends from the handle 212 and an opposite end 242 that is connected to the inside of tip 228. The wire 238 can be pulled (arrow 244) to cause the delivery head 220 to collapse (hidden lines) and evert radially inwardly starting at the tip 228.

Returning to a more detailed discussion of FIGS. 1A through 1E, the operator begins the delivery of the support by pushing the tapered end 230 of the head basket 220 into the valve 16 (e.g., the tricuspid valve) to cause the valve leaflets 14 to spread apart. Because the head-end basket is tapered, by continuing to push, the operator can cause the annulus 18 of the tricuspid valve 16 to conform to a desired shape, typically circular. During insertion, because of its taper, the head-end basket is self-centering. The taper of the basket 220 translates the insertion force in direction 248 in a radial force that causes the annulus 18 to expand and temporarily assume a desired shape (and a larger than final diameter).

As the operator continues to push on the tool, the ring of barbs of the hooks touch and then enter the heart tissue along a ring defined by the outer periphery of the annulus and the sharp free ends of the hooks enter and seat themselves within the tissue, much like fish hooks.

Once the hooks are embedded in the tissue, the operator pulls on the near end 240 of wire 238 to cause the basket 220 to collapse, evert, and be drawn out of the valve 16. Eventually, the everted portion of the basket reaches the valve support 100. By further tugging, the operator causes the body 110 of the support 100 to roll about its central axis (as in the o-ring example mentioned early) which causes the hooks 120 to embed firmly in the tissue of the annulus 18 of the valve 16.

Using a final tug, the operator breaks the connection between the tool 200 and the valve support 100 and removes the tool 200, leaving the valve support 100 in place. As the basket 220 passes the points of connection 246, the forces exerted by the embedded hooks 120 on the support body 110, acting in direction 248, exceed the forces exerted by the withdrawing basket 220 on the support body 110 (through the connections 246), acting in direction 250, thereby causing the connections 246 to release the support 100. The tool 200 is then withdrawn, allowing the valve support 100, along with the annulus 18, to contract to the long-run configuration.

Figure 6A:
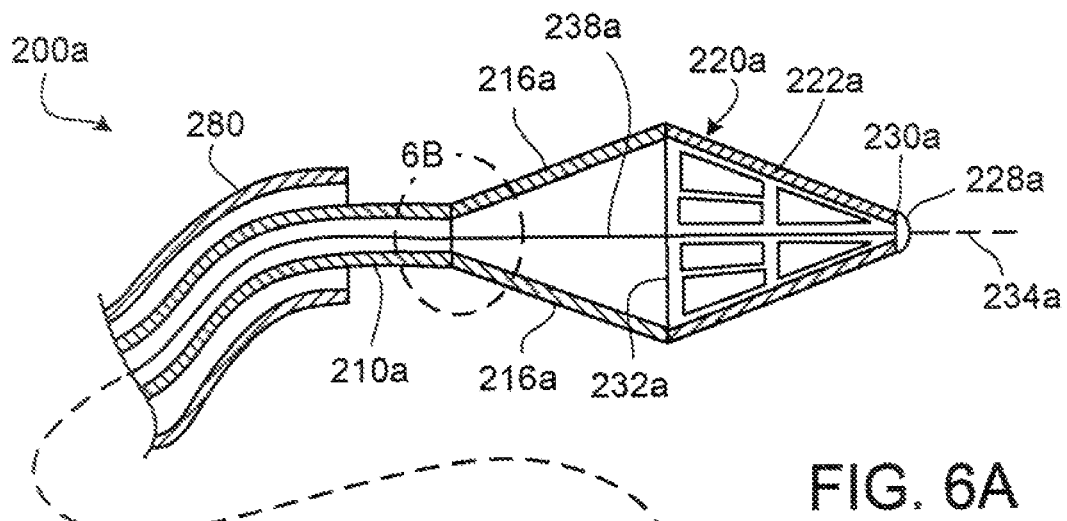
FIGS. 6A and 6B are sectional side views of a catheter delivery tool.
Figure 6A:
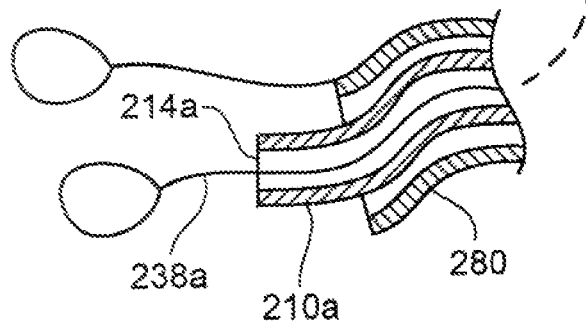

In implementations useful for delivery of the support percutaneously, as shown in FIG. 6A, the delivery head 220a can be made, for example, from a shape memory alloy, such as Nitinol, which will allow the body 222a to be collapsed radially toward the longitudinal axis 234a during delivery of the head from a percutaneous entry point into the heart. The delivery head 220a is biased towards the expanded, tapered orientation shown in FIG. 6A. Thus, the delivery head 220a, in the form of a tapered semi-rigid net, is connected to a catheter shaft 210a through projections 216a that extend radially outwardly from the catheter shaft 210a and taper in a direction opposite the taper of the delivery head 220a.

Figure 6B:
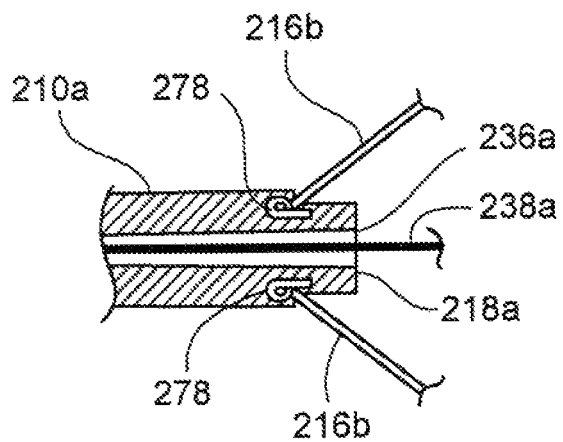

The projections 216a are resiliently mounted to the catheter shaft 210a and are biased towards the tapered orientation shown, for example, by spring biased projections 216b shown in FIG. 6B. The projections 216a include springs 278, e.g., torsion springs (as shown), mounted to the catheter shaft 210a and forming a resilient connection.

A wire 238a slides within a lumen 236a of the shaft 210a in a manner similar to the one described earlier.

The tool 200a also includes a sheath 280 in which the catheter shaft 210a can slide during placement of the support. The sheath 280, the catheter shaft 210a, and the wire 238a are all flexible along their lengths to allow the tool 200a to be deflected and articulated along a blood vessel to reach the heart.

To delivery the support percutaneously, as shown in FIG. 7A, when the delivery head is prepared for use, the sheath 280 is retracted beyond the projections 216a, allowing the delivery head 220a to expand. The valve support 100 is then expanded to the delivery configuration and mounted on the tapered body 222a. The valve support 100 is connected to the delivery head 220a using releasable connections, e.g., breakable sutures and/or retaining elements (as described earlier).

The sheath 280 is then moved along the catheter shaft 210a towards the delivery head 220, causing the projections 216a and the delivery head 220a to contract radially inwardly to fit within the sheath 280, as shown in FIG. 7B. In the contracted configuration, the tip 228a of the delivery head 220a fits against the end 282 of the sheath 280. The rounded tip 228a may provide easier delivery and maneuverability in navigating the blood vessels to reach the heart.

Figure 8B:
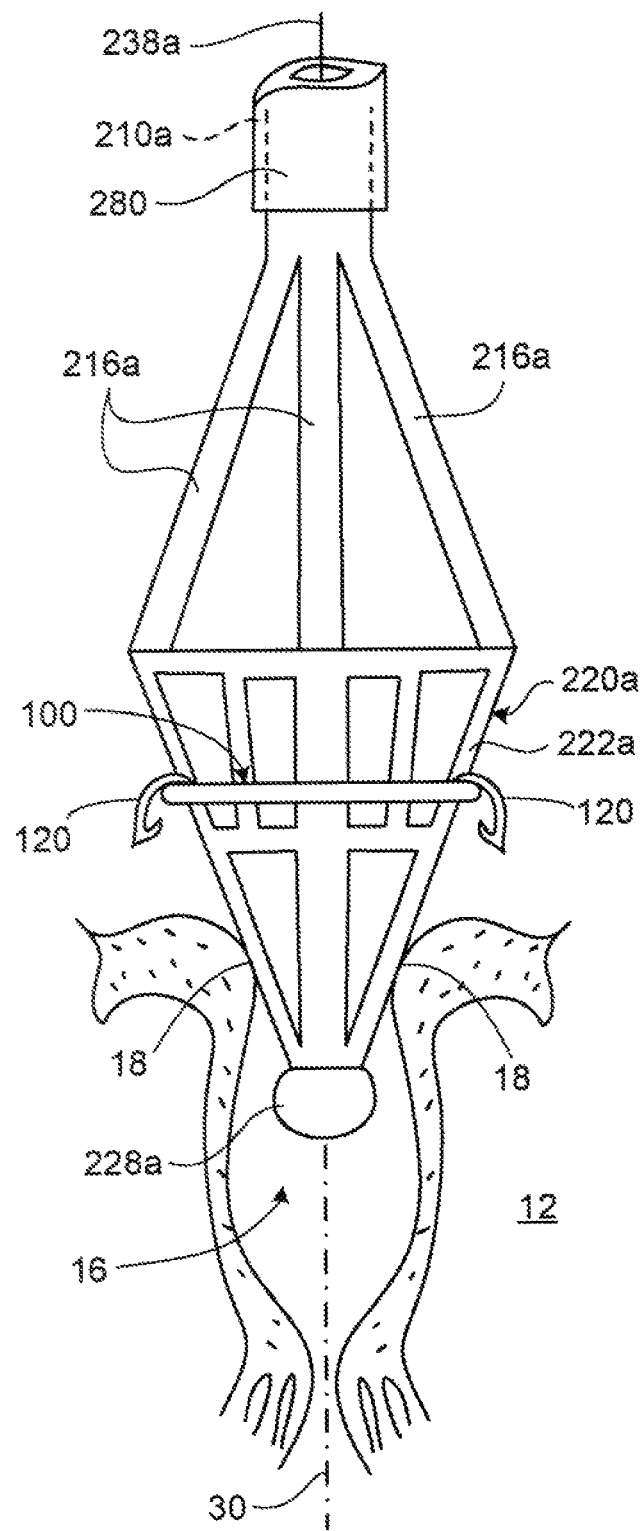

To deliver the support to the valve annulus, the end 230 of the tool 200a is fed percutaneously through blood vessels and into the right atrium 24 (FIG. 8A). The sheath 280 is then retracted, exposing the valve support 100 and allowing the projections 216a, the delivery head 220a, and the support 100 to expand, as shown in FIG. 8A. The catheter shaft 210a is then advanced, e.g., under image guidance, in direction 248a along an axis 30 of the annulus 18. The operator forces the distal end 230a of the self-centering delivery head 220a into the valve 16 (FIG. 8B) using feel or image guidance, without actually seeing the valve 16.

Once the tip is in the valve 16, the operator pushes on the end 214a of the catheter shaft 210a to force the tool further into the valve 16. This causes the tapered body 222a of the delivery head 220a to restore the shape of the annulus 18 to a circle or other desired shape (such as the distinctive "D" shape of a healthy mitral valve). The tool 200a is self-centering because of its shape. The net-like construction of the delivery head 220a (and the head used in open heart surgery, also) allows blood to flow through the valve even while the delivery head 220a is inserted.

Figure 8C:
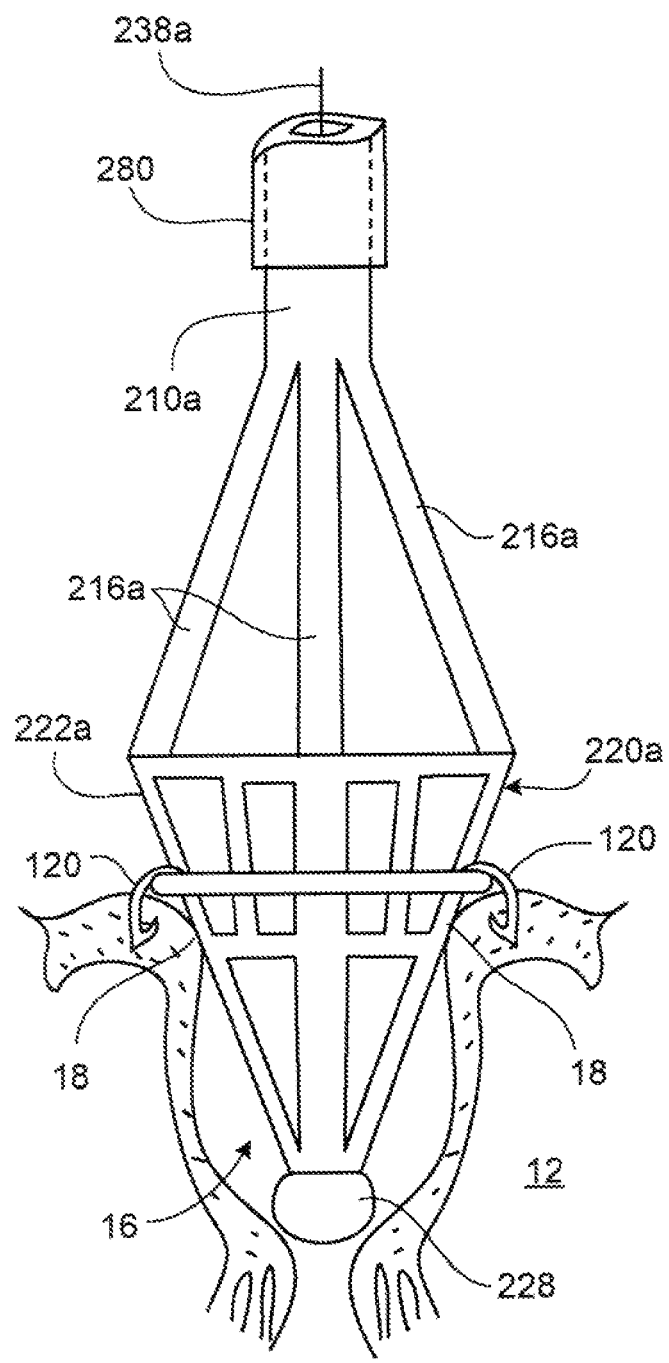

As tool 200a reaches the point at which the support hooks touch the annulus, by giving an additional push, the operator drives the hooks 120 of the valve support 100 together into all of the annular locations at which it is to be attached, as shown in FIG. 8C. The configuration of the valve support 100 and the tool 200a and the manner of temporary attachment of the support 100 to the tool 200a assure that the hooks 120 will penetrate the valve 16 exactly at the correct positions, just along the outer edge of the annulus 18.

Figure 8D:
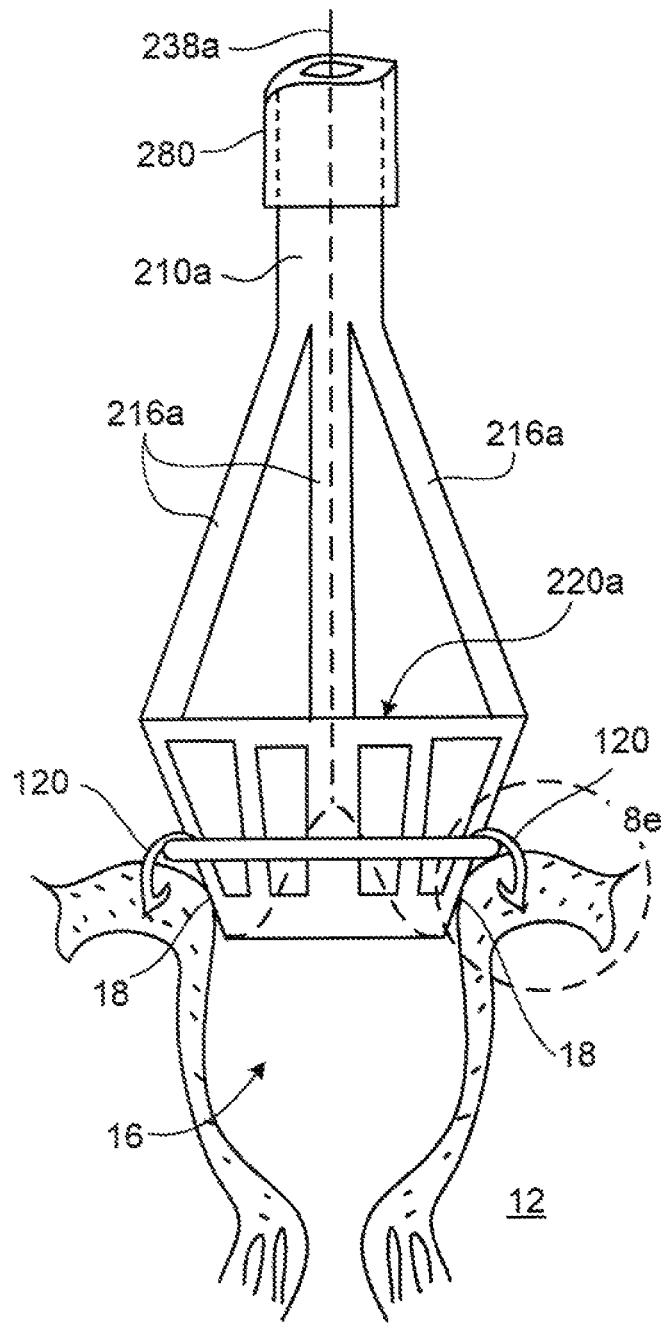
Figure 8E:
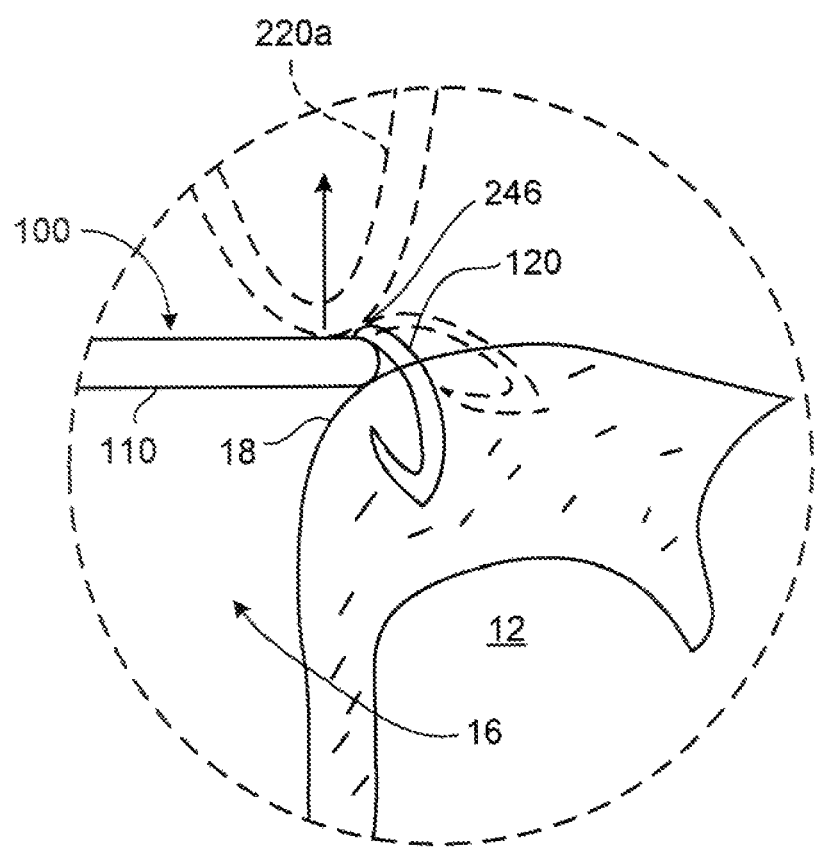

Once the valve support 100 has been attached to the valve 16, the operator pulls on the proximal end 240a causing the delivery head 220a to evert (hidden dashed lines) and be drawn out of the valve 16 (shown in FIG. 8D). Eventually the everted portion of the tool 200a reaches the valve support 100. By further tugging, the operator causes the torus of the support 100 to roll all around its periphery which jams the hooks 120 securely into the annulus 18 of the valve 16, as illustrated in FIG. 8E, seating the support permanently and permitting later growth of tissue around the support 100. The depth and radial extent of each of the placed hooks 120 is essentially the same as a conventional suture so that their placement is likely to be as effective and familiar to the operator and others as conventional sutures.

Figure 8F:
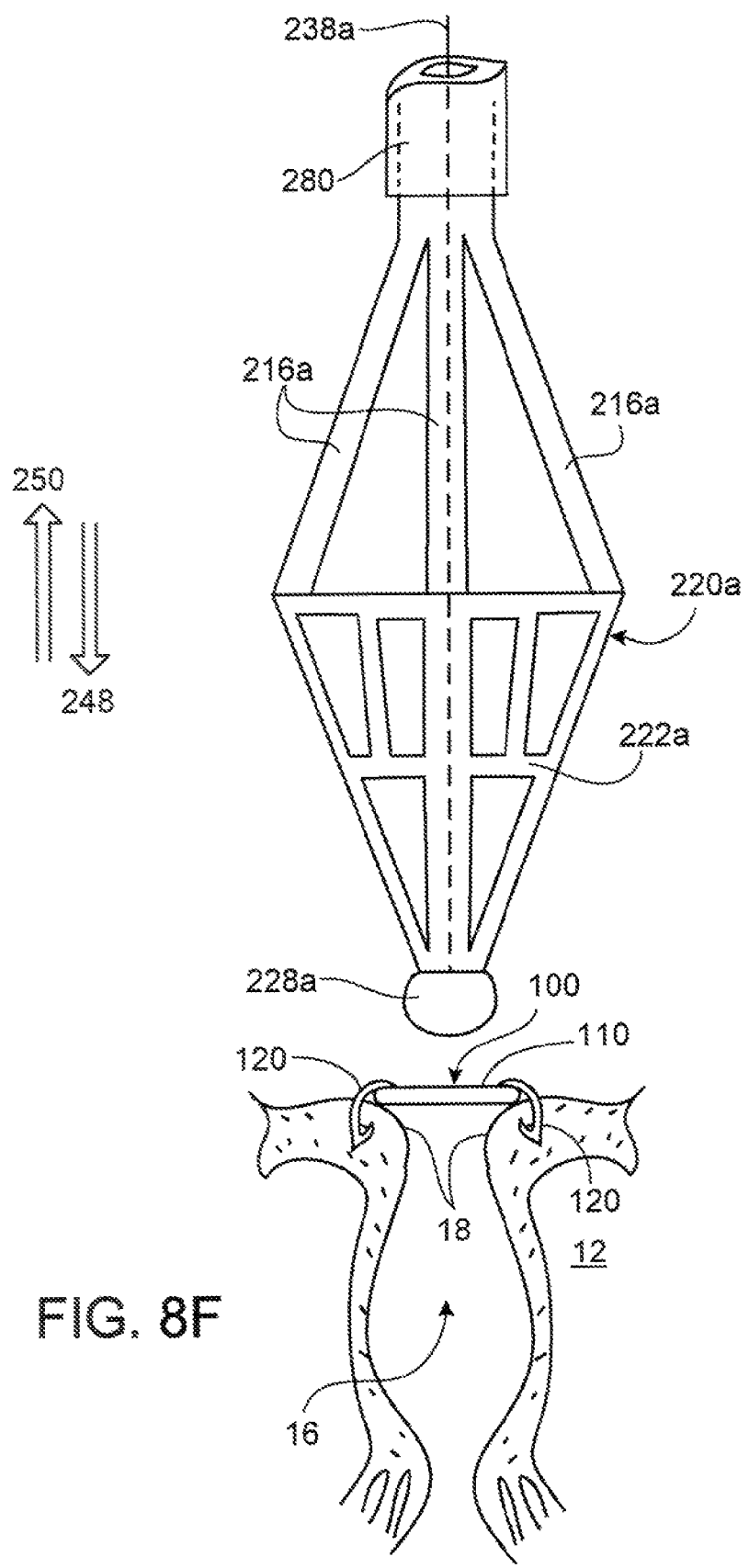
Figure 8G:
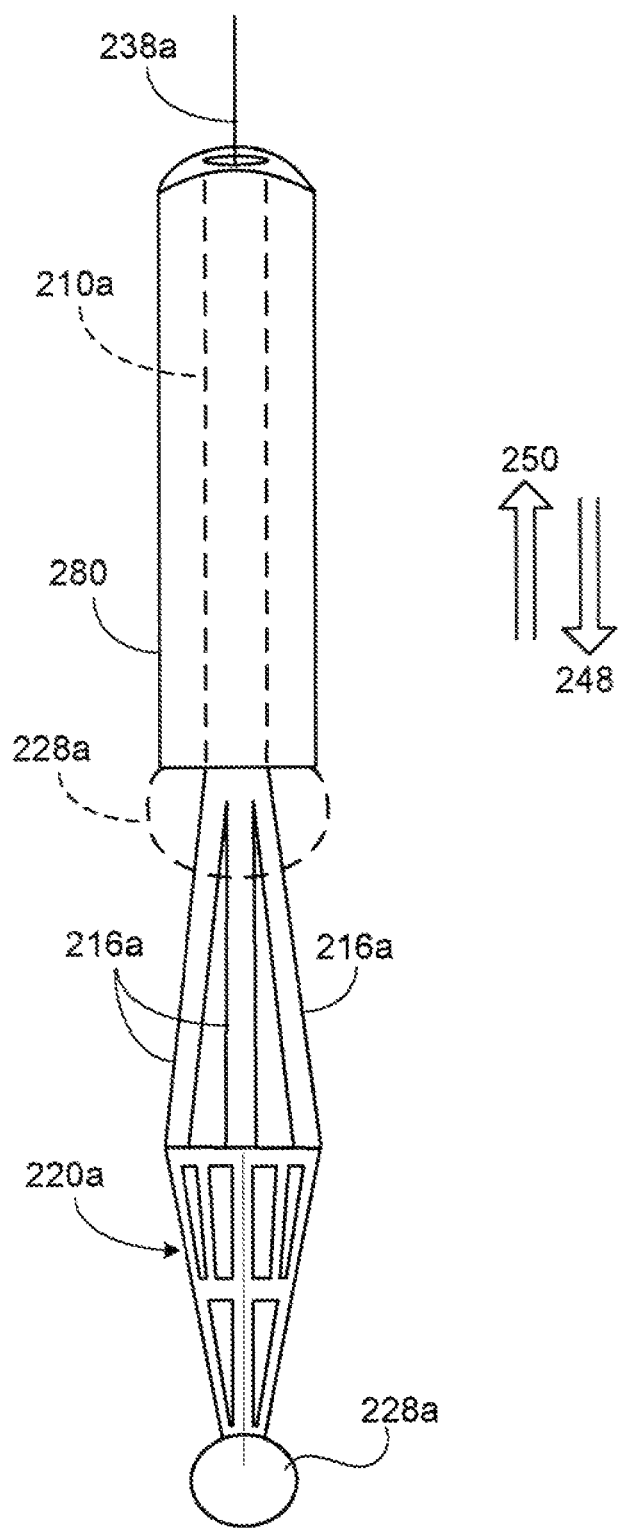

Using a final tug, the operator breaks the connections 246 between the tool 200a and the valve support 100 and retracts the catheter shaft 210, leaving the support 100 in place. The catheter shaft 210 is retracted to a position beyond the valve annulus 18 and the wire is advanced in the first direction allowing the delivery head 220a to assume its original tapered shape (FIG. 8F). The catheter shaft 210a is then retracted into the sheath 280 (FIG. 8G), and the tool 200a is withdrawn.

Figure 8H:
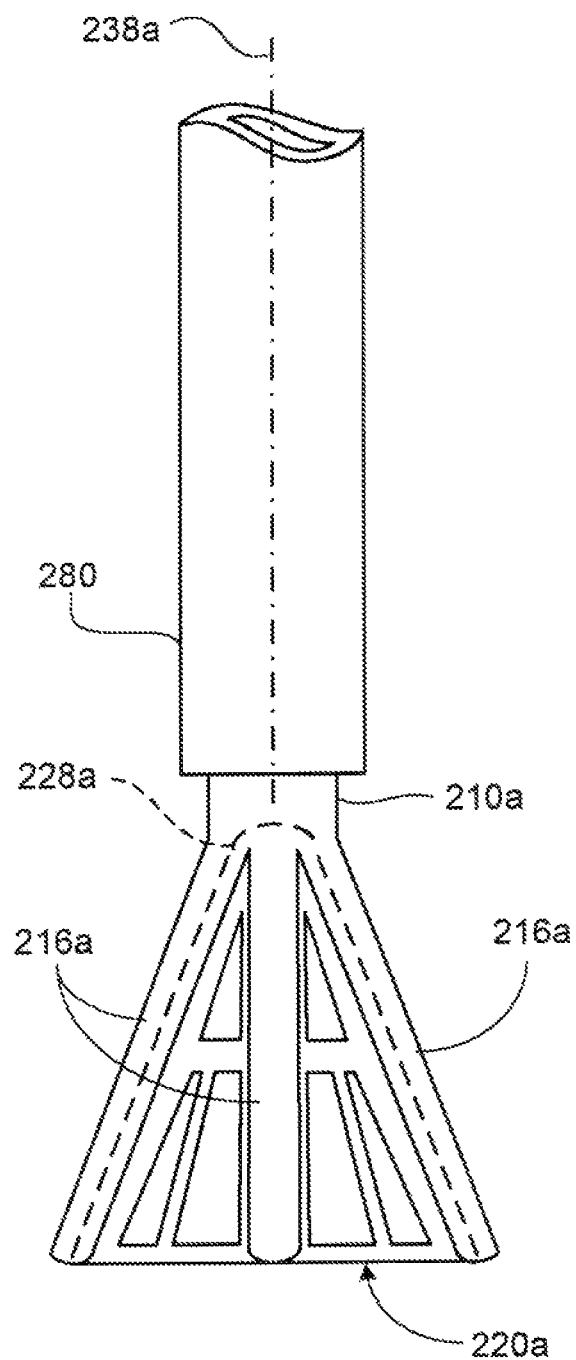
Figure 8I:
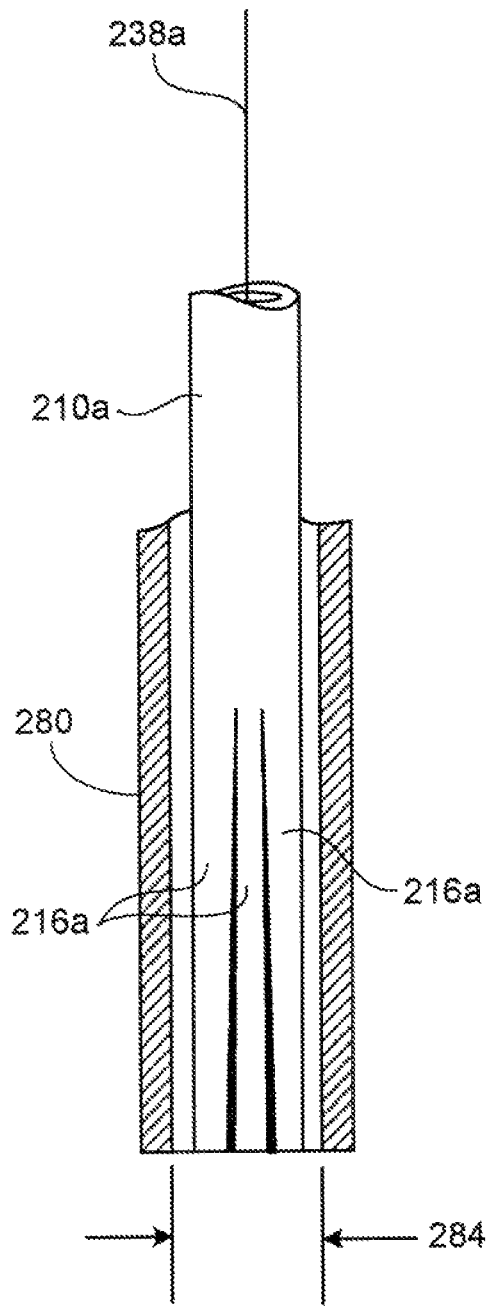

In other examples, as shown in FIGS. 8H and 8I, the tip 228a of the tool 200a has a compressed dimension that is smaller than an internal diameter 284 of the sheath 280, permitting the catheter shaft 210a to be retracted directly into the sheath 280 after deployment, as shown in FIG. 8I.

With the tool 200a withdrawn, the valve support 100 contracts reshaping the annulus 18 such that the valve leaflets 14 coapt to prevent a backflow of blood during systole.

Other implementations are within the scope of the claims.

For example, distortion of either the tricuspid valve or mitral valve can be corrected. For tricuspid valve repair, the hooks can be arranged around only about three-quarters of the support and therefore the annulus. For mitral valve repair, the hooks can cover the entire periphery of the annulus. For mitral valve repair, a back-up valve can be provided as part of the delivery tool to maintain heart function during the delivery procedure. Materials other than shape memory materials may be used as the material for the support body, and other ways can be used to force the support back to a desired size following expansion, including, for example, cross-bars that span the opening of the support.

In addition, the left atrial appendage of the heart can be closed. For example, the tool can be pushed into an opening of an atrial appendage causing the opening to assume a predetermined shape. The tool can be continued to be pushed in order to embed the hooks of the expanded support into the periphery of the opening of the appendage. The tool can then be withdrawn, releasing the support, and allowing the support to contract. The support can have a relatively small contracted diameter such that, when the tool is withdrawn, releasing the support, the support can contract to a relatively small size, effectively closing off the appendage.

In addition to the open heart and percutaneous deployment procedures, the valve support can also be deployed through the chest.

The head of the tool need not be a basket, but can take any form and strength that enables the valve annulus to be forced open to a shape that corresponds to the shape of the support. The basket can be made of a wide variety of materials. The basket can be held and pushed using a wide variety of structural mechanisms that permit both pushing and pulling on the support both to seat and embed the support in the annulus tissue and disconnect the support from the tool.

The tool need not be conical.

The support could take a wide variety of configurations, sizes, and shapes, and be made of a wide variety of materials.

The hooks could be replaced by other devices to seat and embed the support using the pushing force of the tool.

The hooks of the support need not be embedded directly in the annulus but might be embedded in adjacent tissue, for example.

What is claimed is:

1. A method comprising:

causing a catheter to traverse a body lumen to place a delivery tool with a valve support attached to the delivery tool at an annulus of a heart valve, the valve support having a plurality of barbs or hooks attached thereto, and the delivery tool comprising a tapered outer surface having interconnected struts defining apertures;

pushing the delivery tool distally through the annulus from one heart chamber to another heart chamber causing the delivery tool to radially dilate the annulus to a configuration determined by the delivery tool;

while the annulus is dilated, attaching the hooks or barbs into tissue at locations along the annulus;

after the support is attached into the tissue, moving a tip of the delivery tool proximally to rotate the barbs or hooks about the support to embed the barbs or hooks more securely into the tissue; and causing the valve support to contract to a smaller diameter.

2. The method of claim 1, wherein the valve support is expandable and contractable.

3. The method of claim 1, wherein the support comprises at least one of stainless steel, gold, Nitinol, and a biologically compatible elastomer.

4. The method of claim 1 also including sheathing the valve support before the catheter is caused to traverse the body lumen and unsheathing the valve support in the vicinity of the heart valve.

5. The method of claim 4 in which the sheathing and unsheathing include moving the catheter and a sheath relative to one another to cause the valve support to be compressed and expanded, respectively.

6. The method of claim 1, wherein the hooks comprise at least one of platinum, gold, palladium, rhenium, tantalum, tungsten, molybdenum, nickel, cobalt, stainless steel, Nitinol, and alloys thereof.

7. A method comprising:

causing a catheter to traverse a body lumen to place a delivery tool with a valve support attached to the delivery tool at an annulus of a heart valve, the valve support having a plurality of barbs or hooks attached thereto, and the delivery tool comprising a self-expanding, semi-rigid net;

pushing the delivery tool distally through the annulus from one heart chamber to another heart chamber causing the delivery tool to radially dilate the annulus to a configuration determined by the delivery tool;

while the annulus is dilated, attaching the hooks or barbs into tissue at locations along the annulus;

after the support is attached into the tissue, moving a tip of the delivery tool proximally to rotate the barbs or hooks about the support to embed the barbs or hooks more securely into the tissue; and causing the valve support to contract to a smaller diameter.

8. The method of claim 7, wherein the valve support is expandable and contractable.

9. The method of claim 7, wherein the support comprises at least one of stainless steel, gold, Nitinol, and a biologically compatible elastomer.

10. The method of claim 7 also including sheathing the valve support before the catheter is caused to traverse the body lumen and unsheathing the valve support in the vicinity of the heart valve.

11. The method of claim 10 in which the sheathing and unsheathing include moving the catheter and a sheath relative to one another to cause the valve support to be compressed and expanded, respectively.

12. The method of claim 7, wherein the hooks comprise at least one of platinum, gold, palladium, rhenium, tantalum, tungsten, molybdenum, nickel, cobalt, stainless steel, Nitinol, and alloys thereof.

* * * * *

UNITED STATES PATENT AND TRADEMARK OFFICE
CERTIFICATE OF CORRECTION

| | | |
|---|---|---|
| PATENT NO. | : 9,192,471 B2 | Page 1 of 1 |
| APPLICATION NO. | : 11/620955 | |
| DATED | : November 24, 2015 | |
| INVENTOR(S) | : Steven F. Bolling | |

It is certified that error appears in the above-identified patent and that said Letters Patent is hereby corrected as shown below:

On the title page

In column 1 (page 3, item 56) at line 61, Under Other Publications, change "Long-Tenn" to --Long-Term--.

In column 2 (page 3, item 56) at line 17, Under Other Publications, change "Anulus," to --Annulus,--.

In the specification

In column 3 at line 9, Change "annular," to --annulus,--.

In column 3 at line 29, Change "view" to --views--.

In column 3 at line 51, Change "expander" to --expanded--.

In column 4 at line 25, Change "health" to --healthy--.

In column 4 at line 43, Change "delivery," to --deliver,--.

In column 6 at line 32, Change "in" to --into--.

In column 6 at line 46, Change "early)" to --earlier)--.

In column 7 at line 18, Change "delivery" to --deliver--.

Signed and Sealed this
Seventh Day of June, 2016

Michelle K. Lee
*Director of the United States Patent and Trademark Office*